(12) United States Patent
Taniike et al.

(10) Patent No.: US 11,142,553 B2
(45) Date of Patent: Oct. 12, 2021

(54) PROTEIN COMPOSITION, METHOD FOR PRODUCING SAME AND METHOD FOR IMPROVING HEAT STABILITY

(71) Applicants: Spiber Inc., Yamagata (JP); Kojima Industries Corporation, Aichi (JP)

(72) Inventors: Toshiaki Taniike, Nomi (JP); Anh Thi Ngoc Dao, Nomi (JP); Koyuru Nakayama, Nomi (JP); Junichi Shimokata, Tsuruoka (JP); Kengo Takeuchi, Toyota (JP); Abhijit Ravikiran Muley, Tsuruoka (JP); Sunita Darbe, Tsuruoka (JP)

(73) Assignees: Spiber Inc., Yamagata (JP); Kojima Industries Corporation, Aichi (JP)

( * ) Notice: Subject to any disclaimer, the term of this patent is extended or adjusted under 35 U.S.C. 154(b) by 0 days.

(21) Appl. No.: 16/463,470

(22) PCT Filed: Nov. 29, 2017

(86) PCT No.: PCT/JP2017/042896
§ 371 (c)(1),
(2) Date: May 23, 2019

(87) PCT Pub. No.: WO2018/101358
PCT Pub. Date: Jun. 7, 2018

(65) Prior Publication Data
US 2019/0352349 A1    Nov. 21, 2019

(30) Foreign Application Priority Data

Nov. 29, 2016 (JP) .............................. JP2016-231335

(51) Int. Cl.
  *C07K 14/435* (2006.01)
  *C07K 1/00* (2006.01)
(52) U.S. Cl.
  CPC .......... *C07K 14/43518* (2013.01); *C07K 1/00* (2013.01)
(58) Field of Classification Search
  None
  See application file for complete search history.

(56) References Cited

FOREIGN PATENT DOCUMENTS

| GB | 1243539 | 8/1971 |
|---|---|---|
| JP | H02-042982 A | 2/1990 |
| JP | H03-112903 A | 5/1991 |
| JP | H05-051397 A | 3/1993 |
| JP | H05-065296 A | 3/1993 |
| JP | H07-090182 A | 4/1995 |
| JP | H08-113714 A | 5/1996 |
| JP | H10-330400 A | 12/1998 |
| JP | 2001-057851 A | 3/2001 |
| JP | 2006-143668 A | 6/2006 |
| JP | 2011-177128 A | 9/2011 |
| WO | 02/060491 A2 | 8/2002 |
| WO | 2004/057068 A1 | 7/2004 |
| WO | 2006/066987 A1 | 6/2006 |
| WO | 2009/074352 A1 | 6/2009 |
| WO | 2010/017282 A1 | 2/2010 |
| WO | 2010/030670 A2 | 3/2010 |
| WO | 2010/042798 A2 | 4/2010 |
| WO | 2011/134979 A2 | 11/2011 |
| WO | 2016/020210 A1 | 2/2016 |
| WO | WO-2016020210 A1 * | 2/2016 ............. A61K 38/37 |

OTHER PUBLICATIONS

Sheng et al., "Vitamin E-loaded silk fibroin nanofibrous mats fabricated by green process for skin care application," International Journal of Biological Macromolecules, 56: 49-56 (2013).
Extended European Search Report issued in counterpart European Patent Application No. 17877121.8 dated Sep. 22, 2020.
International Preliminary Report on Patentability and Written Opinion issued in corresponding International Patent Application No. PCT/JP2017/042896 dated Jun. 13, 2019.
International Search Report issued in corresponding International Patent Application No. PCT/JP2017/042896 dated Feb. 20, 2018.
Luo et al., "Stabilization of Natural Antioxidants by Silk Biomaterials," ACS Applied Materials & Interfaces, 8: 13573-13582 (2016).
Shigeyoshi Osaki, "Spider Tread-Its Protein Science," 41 (14) (1996).
Kasoju et al., "Fabrication and characterization of curcumin-releasing silk fibroin scaffold," Journal of Biomedical Materials Research, Part B: Applied Biomaterials, 100B: 1854-1866 (2012).
Partial Supplementary European Search Report issued in counterpart European Patent Application No. 17877121.8 dated Jun. 23, 2020.

* cited by examiner

*Primary Examiner* — Anand U Desai
(74) *Attorney, Agent, or Firm* — Morgan, Lewis & Bockius LLP

(57) ABSTRACT

The present invention relates to a protein composition formed of dry matter of a dispersion in which a protein is dispersed in a stabilizer solution, in which the stabilizer includes at least one type selected from the group consisting of a catechol-based stabilizer, 6-hydroxy-2,5,7,8-tetramethylchroman-2-carboxylic acid, 2,6-di-tert-butyl-p-cresol, 2-tert-butyl-4-methoxyphenol, and 6,6'-di-tert-butyl-4,4'-butylidenedi-m-cresol.

16 Claims, 2 Drawing Sheets

Specification includes a Sequence Listing.

(a)

(b)

(c)

```
                       SEQUENCE LISTING

<160> NUMBER OF SEQ ID NOS: 6

<210> SEQ ID NO 1
<211> LENGTH: 601
<212> TYPE: PRT
<213> ORGANISM: Artificial Sequence
<220> FEATURE:
<223> OTHER INFORMATION: PRT410

<400> SEQUENCE: 1

Met His His His His His His Ser Ser Gly Ser Ser Gly Pro Gly Gln
1               5                   10                  15

Gln Gly Pro Tyr Gly Pro Gly Ala Ser Ala Ala Ala Ala Ala Gly Gln
                20                  25                  30

Asn Gly Pro Gly Ser Gly Gln Gln Gly Pro Gly Gln Ser Gly Gln Tyr
            35                  40                  45

Gly Pro Gly Gln Gln Gly Pro Gly Gln Gln Gly Pro Gly Ser Ser Ala
        50                  55                  60

Ala Ala Ala Ala Gly Pro Gly Gln Tyr Gly Pro Gly Gln Gln Gly Pro
65                  70                  75                  80

Ser Ala Ser Ala Ala Ala Ala Ala Gly Pro Gly Ser Gly Gln Gln Gly
                85                  90                  95

Pro Gly Ala Ser Gly Gln Tyr Gly Pro Gly Gln Gln Gly Pro Gly Gln
            100                 105                 110

Gln Gly Pro Gly Ser Ser Ala Ala Ala Ala Gly Gln Tyr Gly Ser
        115                 120                 125

Gly Pro Gly Gln Gln Gly Pro Tyr Gly Ser Ala Ala Ala Ala Ala Gly
    130                 135                 140

Pro Gly Ser Gly Gln Tyr Gly Gln Gly Pro Tyr Gly Pro Gly Ala Ser
145                 150                 155                 160

Gly Pro Gly Gln Tyr Gly Pro Gly Gln Gln Gly Pro Ser Ala Ser Ala
                165                 170                 175

Ala Ala Ala Gly Ser Gly Gln Gln Gly Pro Gly Gln Tyr Gly Pro
            180                 185                 190

Tyr Ala Ser Ala Ala Ala Ala Gly Gln Tyr Gly Ser Gly Pro Gly
        195                 200                 205

Gln Gln Gly Pro Tyr Gly Pro Gly Gln Ser Gly Ser Gly Gln Gln Gly
        210                 215                 220

Pro Gly Gln Gln Gly Pro Tyr Ala Ser Ala Ala Ala Ala Gly Pro
225                 230                 235                 240
```

Gly Gln Gln Gly Pro Tyr Gly Pro Gly Ser Ala Ala Ala Ala
            245                 250                 255

Gly Gln Tyr Gly Tyr Gly Pro Gln Gln Gly Pro Tyr Gly Pro Gly
        260                 265                 270

Ala Ser Gly Gln Asn Gly Pro Gly Ser Gly Gln Tyr Gly Pro Gly Gln
        275                 280                 285

Gln Gly Pro Gly Gln Ser Ala Ala Ala Gly Pro Gly Gln Gln
        290                 295                 300

Gly Pro Tyr Gly Pro Ala Ser Ala Ala Ala Ala Gly Gln Tyr
305                 310                 315                 320

Gly Pro Gly Gln Gln Gly Pro Gly Gln Tyr Gly Pro Gly Ser Ser Gly
                325                 330                 335

Pro Gly Gln Gln Gly Pro Tyr Gly Pro Gly Ser Ser Ala Ala Ala Ala
                340                 345                 350

Ala Gly Gln Tyr Gly Pro Gly Gln Gln Gly Pro Tyr Gly Pro Gly Gln
                355                 360                 365

Ser Ala Ala Ala Ala Gly Gln Tyr Gln Gly Pro Gly Gln Gln
            370                 375                 380

Gly Pro Tyr Gly Pro Gly Ala Ser Gly Pro Gly Gln Gln Gly Pro Tyr
385                 390                 395                 400

Gly Pro Gly Ala Ser Ala Ala Ala Ala Gly Pro Gly Gln Tyr Gly
                405                 410                 415

Pro Gly Gln Gln Gly Pro Ser Ala Ser Ala Ala Ala Ala Gly Gln
                420                 425                 430

Tyr Gly Ser Gly Pro Gly Gln Tyr Gly Pro Tyr Gly Pro Gly Gln Ser
        435                 440                 445

Gly Pro Gly Ser Gly Gln Gln Gly Gln Gly Pro Tyr Gly Pro Gly Ala
    450                 455                 460

Ser Ala Ala Ala Ala Gly Gln Tyr Gly Pro Gln Gln Gly Pro
465                 470                 475                 480

Tyr Gly Pro Gly Gln Ser Ala Ala Ala Ala Gly Pro Gly Ser Gly
                485                 490                 495

Gln Tyr Gly Pro Gly Ala Ser Gly Gln Asn Gly Pro Gly Ser Gly Gln
        500                 505                 510

Tyr Gly Pro Gly Gln Gln Gly Pro Gly Gln Ser Ala Ala Ala Ala
        515                 520                 525

Gly Gln Tyr Gln Gln Gly Pro Gly Gln Gln Gly Pro Tyr Gly Pro Gly
    530                 535                 540

Ala Ser Ala Ala Ala Ala Ala Gly Gln Tyr Gly Ser Gly Pro Gly Gln
545                 550                 555                 560

Gln Gly Pro Tyr Gly Pro Gly Gln Ser Gly Ser Gly Gln Gln Gly Pro
            565                 570                 575

Gly Gln Gln Gly Pro Tyr Ala Ser Ala Ala Ala Ala Gly Pro Gly
            580                 585                 590

Ser Gly Gln Gln Gly Pro Gly Ala Ser
        595                 600

<210> SEQ ID NO 2
<211> LENGTH: 559
<212> TYPE: PRT
<213> ORGANISM: Artificial
<220> FEATURE:
<223> OTHER INFORMATION: PRT215

<400> SEQUENCE: 2

-continued

```
Met His His His His His His His His Ser Ser Gly Ser Ser
1               5                   10                  15

Leu Glu Val Leu Phe Gln Gly Pro Gly Ala Gly Gly Ser Gly Pro Gly
            20                  25                  30

Gly Ala Gly Pro Gly Gly Val Gly Pro Gly Gly Ser Gly Pro Gly Gly
                35                  40                  45

Val Gly Pro Gly Gly Ser Gly Pro Gly Gly Val Gly Pro Gly Gly Ser
50                  55                  60

Gly Pro Gly Gly Val Gly Pro Gly Gly Ala Gly Pro Tyr Gly Pro
65                  70                  75                  80

Gly Gly Ser Gly Pro Gly Gly Ala Gly Ala Gly Pro Gly Gly
                85                  90                  95

Ala Tyr Gly Pro Gly Gly Ser Tyr Gly Pro Gly Gly Ser Gly Gly Pro
                100                 105                 110

Gly Gly Ala Gly Gly Pro Tyr Gly Pro Gly Gly Glu Gly Pro Gly Gly
            115                 120                 125

Ala Gly Gly Pro Tyr Gly Pro Gly Gly Ala Gly Pro Tyr Gly Pro
        130                 135                 140

Gly Gly Ala Gly Gly Pro Tyr Gly Pro Gly Gly Glu Gly Gly Pro Tyr
145                 150                 155                 160

Gly Pro Gly Gly Ser Tyr Gly Pro Gly Gly Ala Gly Pro Tyr Gly
                165                 170                 175

Pro Gly Gly Pro Tyr Gly Pro Gly Gly Glu Gly Pro Gly Ala Gly
            180                 185                 190

Gly Pro Tyr Gly Pro Gly Gly Val Gly Pro Gly Gly Gly Pro Gly
        195                 200                 205

Gly Tyr Gly Pro Gly Gly Ala Gly Pro Gly Gly Tyr Gly Pro Gly Gly
    210                 215                 220

Ser Gly Pro Gly Gly Tyr Gly Pro Gly Gly Ser Gly Pro Gly Gly Tyr
225                 230                 235                 240

Gly Pro Gly Gly Ser Gly Pro Gly Gly Tyr Gly Pro Gly Gly Ser Gly
                245                 250                 255

Pro Gly Gly Tyr Gly Pro Gly Gly Ser Gly Pro Gly Gly Ser Gly Pro
            260                 265                 270

Gly Gly Tyr Gly Pro Gly Gly Ser Gly Pro Gly Gly Ser Gly Pro Gly
        275                 280                 285

Gly Tyr Gly Pro Gly Gly Ser Gly Pro Gly Gly Tyr Gly Pro Gly Gly
    290                 295                 300

Ser Gly Pro Gly Gly Ser Gly Pro Gly Gly Tyr Gly Pro Gly Gly Ser
305                 310                 315                 320

Gly Pro Gly Gly Ser Gly Pro Gly Gly Tyr Gly Pro Gly Gly Ser Gly
                325                 330                 335

Pro Gly Gly Phe Gly Pro Gly Gly Phe Gly Pro Gly Gly Ser Gly Pro
            340                 345                 350

Gly Gly Tyr Gly Pro Gly Gly Ser Gly Pro Gly Gly Ala Gly Pro Gly
        355                 360                 365

Gly Val Gly Pro Gly Gly Phe Gly Pro Gly Gly Ala Gly Pro Gly Gly
    370                 375                 380

Ala Gly Pro Gly Gly Ala Gly Pro Gly Gly Ala Gly Pro Gly Gly Ala
385                 390                 395                 400

Gly Pro Gly Gly Ala Gly Pro Gly Gly Ala Gly Pro Gly Gly Ala Gly
                405                 410                 415

Pro Gly Gly Ala Gly Gly Ala Gly Gly Ala Gly Gly Ala Gly Gly Ser
```

```
                420             425             430
Gly Gly Ala Gly Gly Ser Gly Gly Thr Thr Ile Ile Glu Asp Leu Asp
            435             440             445
Ile Thr Ile Asp Gly Ala Asp Gly Pro Ile Thr Ile Ser Glu Glu Leu
450             455             460
Thr Ile Ser Ala Tyr Tyr Pro Ser Ser Arg Val Pro Asp Met Val Asn
465             470             475             480
Gly Ile Met Ser Ala Met Gln Gly Ser Gly Phe Asn Tyr Gln Met Phe
            485             490             495
Gly Asn Met Leu Ser Gln Tyr Ser Ser Gly Ser Gly Thr Cys Asn Pro
            500             505             510
Asn Asn Val Asn Val Leu Met Asp Ala Leu Leu Ala Ala Leu His Cys
            515             520             525
Leu Ser Asn His Gly Ser Ser Phe Ala Pro Ser Pro Thr Pro Ala
            530             535             540
Ala Met Ser Ala Tyr Ser Asn Ser Val Gly Arg Met Phe Ala Tyr
545             550             555

<210> SEQ ID NO 3
<211> LENGTH: 252
<212> TYPE: PRT
<213> ORGANISM: Artificial Sequence
<220> FEATURE:
<223> OTHER INFORMATION: Collagen-type4-Kai

<400> SEQUENCE: 3

Met His His His His His Ser Ser Gly Ser Ser Lys Asp Gly Val
1               5              10              15
Pro Gly Phe Pro Gly Ser Glu Gly Val Lys Gly Asn Arg Gly Phe Pro
            20              25              30
Gly Leu Met Gly Glu Asp Gly Ile Lys Gly Gln Lys Gly Asp Ile Gly
            35              40              45
Pro Pro Gly Phe Arg Gly Pro Thr Glu Tyr Tyr Asp Thr Tyr Gln Glu
    50              55              60
Lys Gly Asp Glu Gly Thr Pro Gly Pro Pro Gly Arg Gly Ala Arg
65              70              75              80
Gly Pro Gln Gly Pro Ser Gly Pro Gly Val Pro Gly Ser Pro Gly
            85              90              95
Ser Ser Arg Pro Gly Leu Arg Gly Ala Pro Gly Trp Pro Gly Leu Lys
            100             105             110
Gly Ser Lys Gly Glu Arg Gly Arg Pro Gly Lys Asp Ala Met Gly Thr
            115             120             125
Pro Gly Ser Pro Gly Cys Ala Gly Ser Pro Gly Leu Pro Gly Ser Pro
        130             135             140
Gly Pro Pro Gly Pro Pro Gly Asp Ile Val Phe Arg Lys Gly Pro Pro
145             150             155             160
Gly Asp His Gly Leu Pro Gly Tyr Leu Gly Ser Pro Gly Ile Pro Gly
            165             170             175
Val Asp Gly Pro Lys Gly Glu Pro Gly Leu Leu Cys Thr Gln Cys Pro
            180             185             190
Tyr Ile Pro Gly Pro Pro Gly Leu Pro Gly Leu Pro Gly Leu His Gly
            195             200             205
Val Lys Gly Ile Pro Gly Arg Gln Gly Ala Ala Gly Leu Lys Gly Ser
        210             215             220
Pro Gly Ser Pro Gly Asn Thr Gly Leu Pro Gly Phe Pro Gly Phe Pro
```

```
            225                 230                 235                 240

Gly Ala Gln Gly Asp Pro Gly Leu Lys Gly Glu Lys
                    245                 250

<210> SEQ ID NO 4
<211> LENGTH: 310
<212> TYPE: PRT
<213> ORGANISM: Artificial Sequence
<220> FEATURE:
<223> OTHER INFORMATION: Resilin-Kai

<400> SEQUENCE: 4

Met His His His His His Pro Glu Pro Val Asn Ser Tyr Leu
1               5                   10                  15

Pro Pro Ser Asp Ser Tyr Gly Ala Pro Gly Gln Ser Gly Pro Gly Gly
                20                  25                  30

Arg Pro Ser Asp Ser Tyr Gly Ala Pro Gly Gly Asn Gly Gly Arg
                35                  40                  45

Pro Ser Asp Ser Tyr Gly Ala Pro Gly Gln Gly Gln Gly Gln
    50                  55                  60

Gly Gln Gly Gly Tyr Ala Gly Lys Pro Ser Asp Ser Tyr Gly Ala Pro
65                  70                  75                  80

Gly Gly Gly Asp Gly Asn Gly Arg Pro Ser Ser Tyr Gly Ala
                85                  90                  95

Pro Gly Gly Asn Gly Gly Arg Pro Ser Asp Thr Tyr Gly Ala Pro
                100                 105                 110

Gly Gly Gly Asn Gly Gly Arg Pro Ser Asp Thr Tyr Gly Ala Pro Gly
                115                 120                 125

Gly Gly Asn Gly Asn Gly Arg Pro Ser Ser Ser Tyr Gly Ala
    130                 135                 140

Pro Gly Gln Gly Gln Gly Asn Gly Asn Gly Gly Arg Pro Ser Ser Ser
145                 150                 155                 160

Tyr Gly Ala Pro Gly Gly Asn Gly Gly Arg Pro Ser Asp Thr Tyr
                165                 170                 175

Gly Ala Pro Gly Gly Gly Asn Gly Gly Arg Pro Ser Asp Thr Tyr Gly
                180                 185                 190

Ala Pro Gly Gly Gly Asn Asn Gly Gly Arg Pro Ser Ser Tyr Gly
                195                 200                 205

Ala Pro Gly Gly Gly Asn Gly Gly Arg Pro Ser Asp Thr Tyr Gly Ala
                210                 215                 220

Pro Gly Gly Gly Asn Gly Asn Gly Ser Gly Gly Arg Pro Ser Ser Ser
225                 230                 235                 240

Tyr Gly Ala Pro Gly Gln Gly Gln Gly Phe Gly Gly Arg Pro Ser
                245                 250                 255

Asp Ser Tyr Gly Ala Pro Gly Gln Asn Gln Lys Pro Ser Asp Ser Tyr
                260                 265                 270

Gly Ala Pro Gly Ser Gly Asn Gly Asn Gly Gly Arg Pro Ser Ser Ser
                275                 280                 285

Tyr Gly Ala Pro Gly Ser Gly Pro Gly Gly Arg Pro Ser Asp Ser Tyr
                290                 295                 300

Gly Pro Pro Ala Ser Gly
305                 310

<210> SEQ ID NO 5
<211> LENGTH: 282
<212> TYPE: PRT
```

<213> ORGANISM: Artificial Sequence
<220> FEATURE:
<223> OTHER INFORMATION: elastin short

<400> SEQUENCE: 5

```
Met His His His His His His Ser Ser Gly Ser Ser Leu Gly Val Ser
1               5                   10                  15

Ala Gly Ala Val Val Pro Gln Pro Gly Ala Gly Val Lys Pro Gly Lys
            20                  25                  30

Val Pro Gly Val Gly Leu Pro Gly Val Tyr Pro Gly Gly Val Leu Pro
            35                  40                  45

Gly Ala Arg Phe Pro Gly Val Gly Val Leu Pro Gly Val Pro Thr Gly
        50                  55                  60

Ala Gly Val Lys Pro Lys Ala Pro Gly Val Gly Gly Ala Phe Ala Gly
65                  70                  75                  80

Ile Pro Gly Val Gly Pro Phe Gly Gly Pro Gln Pro Gly Val Pro Leu
                85                  90                  95

Gly Tyr Pro Ile Lys Ala Pro Lys Leu Pro Gly Gly Tyr Gly Leu Pro
            100                 105                 110

Tyr Thr Thr Gly Lys Leu Pro Tyr Gly Tyr Gly Pro Gly Gly Val Ala
            115                 120                 125

Gly Ala Ala Gly Lys Ala Gly Tyr Pro Thr Gly Thr Gly Val Gly Pro
        130                 135                 140

Gln Ala Ala Ala Ala Ala Ala Lys Ala Ala Lys Phe Gly Ala
145                 150                 155                 160

Gly Ala Ala Gly Val Leu Pro Gly Val Gly Gly Ala Gly Val Pro Gly
                165                 170                 175

Val Pro Gly Ala Ile Pro Gly Ile Gly Gly Ile Ala Gly Val Gly Thr
            180                 185                 190

Pro Ala Ala Ala Ala Ala Ala Ala Ala Lys Ala Ala Lys Tyr
            195                 200                 205

Gly Ala Ala Gly Leu Val Pro Gly Gly Pro Gly Phe Gly Pro Gly
        210                 215                 220

Val Val Gly Val Pro Gly Ala Gly Val Pro Gly Val Gly Val Pro Gly
225                 230                 235                 240

Ala Gly Ile Pro Val Val Pro Gly Ala Gly Ile Pro Gly Ala Ala Val
            245                 250                 255

Pro Gly Val Val Ser Pro Glu Ala Ala Ala Lys Ala Ala Ala Lys Ala
            260                 265                 270

Ala Lys Tyr Gly Ala Arg Pro Gly Val Gly
            275                 280
```

<210> SEQ ID NO 6
<211> LENGTH: 12
<212> TYPE: PRT
<213> ORGANISM: Artificial Sequence
<220> FEATURE:
<223> OTHER INFORMATION: His Tag

<400> SEQUENCE: 6

```
Met His His His His His His Ser Ser Gly Ser Ser
1               5                   10
```

PROTEIN COMPOSITION, METHOD FOR PRODUCING SAME AND METHOD FOR IMPROVING HEAT STABILITY

SEQUENCE LISTING SUBMISSION VIA EFS-WEB

A computer readable text file, entitled "SequenceListing.txt," created on or about May 24, 2019 with a file size of about 18 kb contains the sequence listing for this application and is hereby incorporated by reference in its entirety.

TECHNICAL FIELD

The present invention relates to a protein composition, a method for producing the same, and a method for improving heat stability.

BACKGROUND ART

Studies are being conducted into the design and production of new materials, and industrial materialization processes which utilize the superiority of structural proteins represented by spider silk. In the development of materials with a view toward industrialization, deterioration resistance (durability) and stability are important but, in particular, it is difficult to select a stabilizer with regard to the thermal degradation of proteins due to factors such as the ambiguity of the degradation mechanism. In addition, with regard to stabilizers, although there is a large amount of information on hydrophobic resins, for proteins with completely different properties from hydrophobic resins, the molecular structures of effective stabilizers and the process of adding the stabilizers are still unclear. A description is given of the heat resistance of natural spider silk, for example, in Non-Patent Literature 1.

CITATION LIST

Non Patent Literature

[Non-Patent Literature 1] Protein, nucleic acid and enzyme Vol. 41, No. 14 (1996)

SUMMARY OF INVENTION

Technical Problem

Therefore, an object of the present invention is to provide a protein composition with improved heat stability, a method for producing the same, and a method for improving heat stability of a protein.

Solution to Problem

The present invention provides a protein composition (protein composition 1) comprising dry matter of a dispersion in which a protein is dispersed in a stabilizer solution, in which the stabilizer comprises at least one type selected from the group consisting of a catechol-based stabilizer, 6-hydroxy-2,5,7,8-tetramethylchroman-2-carboxylic acid, 2,6-di-tert-butyl-p-cresol, 2-tert-butyl-4-methoxyphenol, and 6,6'-di-tert-butyl-4,4'-butylidenedi-m-cresol.

The present invention also provides a protein composition (protein composition 2) comprising dry matter of a solution in which a protein and a stabilizer are dissolved, in which the stabilizer comprises at least one type selected from the group consisting of N,N'-hexane-1,6-diyl bis[3-(3,5-di-tert-butyl-4-hydroxyphenyl)propionamide], 1,6-hexanediol bis[3-(3,5-di-tert-butyl-4-hydroxyphenyl)propionate], 6,6'-di-tert-butyl-4,4'-butylidene di-m-cresol, 2,6-di-tert-butyl-p-cresol, 3,9-bis(2,6-di-tert-butyl-4-methylphenoxy)-2,4,8,10-tetraoxa-3,9-diphosphaspiro[5.5]undecane, poly[[6-[(1,1,3,3-tetramethylbutyl)amino]-1,3,5-triazine-2,4-diyl][(2,2,6,6-tetramethyl-4-piperidinyl)imino]-1,6-hexanediyl[(2,2,6,6-tetramethyl-4-piperidinyl)imino]], α-tocopherol, propyl 3,4,5-trihydroxybenzoate and 4,4',4''-(1-methylpropanyl-3-ylidene)tris(6-tert-butyl-m-cresol).

It is possible to obtain the protein compositions 1 and 2 by production methods 1 and 2 below, respectively.

Production method 1: A method for producing a protein composition, comprising a step of obtaining a dispersion by dispersing a protein in a stabilizer solution; and a step of obtaining dry matter by removing volatile components from the dispersion, in which the stabilizer comprises at least one type selected from the group consisting of a catechol-based stabilizer, 6-hydroxy-2,5,7,8-tetramethylchroman-2-carboxylic acid, 2,6-di-tert-butyl-p-cresol, 2-tert-butyl-4-methoxyphenol, and 6,6'-di-tert-butyl-4,4'-butylidene di-m-cresol.

Production method 2: A method for producing a protein composition, comprising a step of obtaining a mixed solution by mixing a protein, a solvent for dissolving the protein, and a stabilizer solution, and a step of obtaining dry matter by removing volatile components from the mixed solution, in which the stabilizer comprises at least one type selected from the group consisting of N,N'-hexane-1,6-diyl bis[3-(3,5-di-tert-butyl-4-hydroxyphenyl)propionamide], 1,6-hexanediol bis[3-(3,5-di-tert-butyl-4-hydroxyphenyl)propionate], 6,6'-di-tert-butyl-4,4'-butylidene di-m-cresol, 2,6-di-tert-butyl-p-cresol, 3,9-bis(2,6-di-tert-butyl-4-methylphenoxy)-2,4,8,10-tetraoxa-3,9-diphosphaspiro[5.5]undecane, poly[[6-[(1,1,3,3-tetramethylbutyl)amino]-1,3,5-triazine-2,4-diyl][(2,2,6,6-tetramethyl-4-piperidinyl)imino]-1,6-hexanediyl[(2,2,6,6-tetramethyl-4-piperidinyl)imino]], α-tocopherol, propyl 3,4,5-trihydroxybenzoate, and 4,4',4''-(1-methylpropanyl-3-ylidene) tris(6-tert-butyl-m-cresol).

Both of the protein compositions 1 and 2 exhibit high heat stability, and are thus able to be effectively utilized as industrial materials. That is, the present invention provides methods for improving heat stability of proteins, such as methods 1 and 2 below.

Method 1: A method for improving heat stability of a protein, comprising obtaining a dispersion by dispersing the protein in a solution in which at least one type of compound selected from the group consisting of a catechol-based stabilizer, 6-hydroxy-2,5,7,8-tetramethylchroman-2-carboxylic acid, 2,6-di-tert-butyl-p-cresol, and 2-tert-butyl-4-methoxyphenol, and 6,6'-di-tert-butyl-4,4'-butylidene di-m-cresol is dissolved, and obtaining dry matter in which the protein and the compound are both present by removing volatile components from the dispersion.

Method 2: A method for improving heat stability of a protein, including obtaining a mixed solution by mixing the protein, a solvent for dissolving the protein, and a solution of at least one type of compound selected from the group consisting of N,N'-hexane-1,6-diyl bis[3-(3,5-di-tert-butyl-4-hydroxyphenyl)propionamide], 1,6-hexanediol bis[3-(3,5-di-tert-butyl-4-hydroxyphenyl)propionate], 6,6'-di-tert-butyl-4,4'-butylidene di-m-cresol, 2,6-di-tert-butyl-p-cresol, 3,9-bis(2,6-di-tert-butyl-4-methylphenoxy)-2,4,8,10-tetraoxa-3,9-diphosphaspiro[5.5]undecane, poly[[$^6$-[(1,1,3,3-tetramethylbutyl)amino]-1,3,5-triazine-2,4-diyl][(2,2,6,6-tetramethyl-4-piperidinyl)imino]-1,6-hexanediyl[(2,2,6,6-tetramethyl-4-piperidinyl)imino]], α-tocopherol, propyl 3,4, 5-trihydroxybenzoate, 4,4',4"-(1-methylpropanyl-3-ylidene)tris(6-tert-butyl-m-cresol), and obtaining dry matter in which the protein and the compound are both present by removing volatile components from the mixed solution.

Advantageous Effects of Invention

According to the present invention, a protein composition with improved heat stability, a method for producing the same, and a method for improving heat stability of a protein are provided.

DESCRIPTION OF EMBODIMENTS

Figure 1:
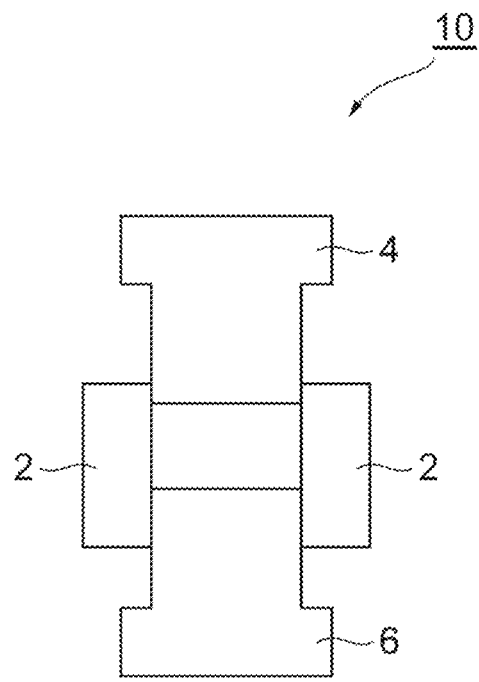
FIG. 1 is a schematic cross-sectional view of a press molding machine.

Hereinafter, a preferred embodiment of the present invention will be described. However, the present invention is not limited to the following embodiment by any means.

The protein composition (protein composition 1) according to the first embodiment is a protein composition containing dry matter of a dispersion in which a protein is dispersed in a stabilizer solution, in which the stabilizer comprises at least one type selected from the group consisting of a catechol-based stabilizer, 6-hydroxy-2,5,7,8-tetramethylchroman-2-carboxylic acid, 2,6-di-tert-butyl-p-cresol, 2-tert-butyl-4-methoxyphenol, and 6,6'-di-tert-butyl-4,4'-butylidene di-m-cresol.

It is possible for the catechol-based stabilizer described above to be at least one type selected from the group consisting of 2-(3,4-dihydroxyphenyl)-3,5,7-trihydroxy-4H-chromen-4-one, (1S,3R,4R,5R)-3-{[3-(3,4-dihydroxyphenyl)acryloyl]oxy}-1,4,5-trihydroxycyclohexane-1-carboxylic acid, 2-(3,4-dihydroxyphenyl)-5,7-dihydroxy-3-{[(2S,3R,4S,5S,6R)-3,4,5-tri hydroxy-6-({[(2R,3R,4R,5R,6S)-3,4,5-trihydroxy-6-methyloxan-2-yl]oxy}methyl)oxan-2-yl]oxy}-4H-chromen-4-one, propyl 3,4,5-trihydroxybenzoate, and 4,4'-(2,3-dimethyl)butane-1,4-diyl)dibenzene-1,2-diol. Below, a combination of these stabilizers and 6-hydroxy-2,5,7,8-tetramethylchroman-2-carboxylic acid, 2,6-di-tert-butyl-p-cresol, 2-tert-butyl-4-methoxyphenol, and 6,6'-di-tert-butyl-4,4'-butylidene di-m-cresol is referred to as a "stabilizer for the first embodiment".

In the protein composition 1, the content of the stabilizer for the first embodiment with respect to 100 parts by mass of protein is preferably more than 0 parts by mass and 10 parts by mass or less, more preferably 0.001 parts by mass or more and 10 parts by mass or less, even more preferably 0.01 parts by mass or more and 5 parts by mass or less, yet more preferably 0.1 parts by mass or more and 2 parts by mass or less, still more preferably 0.1 parts by mass or more and 1 part by mass or less, and still more preferably 0.1 parts by mass or more and 0.5 parts by mass or less. This is because, even when the content is increased to more than 10 parts by mass, the corresponding improvement in heat stability is reduced. It is possible to produce the protein composition 1, for example, using a production method provided with a step of obtaining a dispersion by dispersing a protein in a solution of the stabilizer for the first embodiment, and a step of obtaining dry matter by removing volatile components from the dispersion (production method 1 described above). The protein composition 1 may be a solution in which the dry matter is dissolved in a solvent or the like, or a dispersion in which the dry matter is dispersed in a solvent or the like.

The protein composition 1 may be formed only of the dry matter described above or may contain other components. That is, the protein composition 1 may include other components than the protein and the stabilizer. In addition, when obtaining the protein composition 1, other components may be dissolved in a solvent, and may be added to the dispersion or the dry matter.

Examples of a solvent for producing a solution of the stabilizer for the first embodiment include single solvents such as primary alcohols (e.g. ethanol and methanol), secondary alcohols (e.g. 2-propanol), tertiary alcohols (e.g. tert-butyl alcohol), acetone, methyl ethyl ketone, or dichloromethane, a mixed solvent of at least two of these solvents, or the like. As the solvent, dichloromethane is preferable, a mixed solvent of acetone/methanol at a volume ratio of 1/1 is more preferable, and methanol is even more preferable. This is considered to be because the higher the compatibility of the solvent and the protein, the greater the effect of allowing the stabilizer to enter into the protein molecule, and the greater the improvement of the heat stability effect. The concentration of the stabilizer for the first embodiment in this solution is, for example, 0.1 to 1 mg/ml.

In order to obtain a dispersion, the protein is preferably in powder form. In addition, it is preferable to add the protein to the solution of the stabilizer for the first embodiment in accordance with the above preferable ratio of the protein and the stabilizer for the first embodiment. In the dispersion obtained in this manner, the stabilizer for the first embodiment is dissolved in the solvent, but the protein is dispersed in the solvent. After the addition, it is possible to obtain the protein composition 1 by further stirring and then drying. The stirring time is not particularly limited, and may be, for example, 16 to 60 hours, 16 to 24 hours, or the like at room temperature. The drying method is also not particularly limited, and examples thereof include natural drying (for example, 25° C., 1 atm), reduced pressure drying (for example, 4 hours at 40° C.), or the like.

The protein composition obtained in this manner is typically in powder form or film form. In addition, the dry matter of the protein composition may be an article (a molded article or the like). A production example of the molded article, which is one type of article, is as follows.

That is, it is possible to obtain the molded article by introducing the protein composition 1 into a mold and performing forming and the like, and it is possible to carry out heating and pressing in the forming step. It is possible for the protein composition 1 which is the target of the forming to be in powder form (lyophilized powder or the like) or to have a fibrous (fiber obtained by spinning or the like) shape. In addition, it is possible for the molded article to be a fused article of the protein composition with the above forms.

A description will be given of a method for creating a molded article using a press molding machine (mold) using the drawings. A press molding machine 10 shown in FIG. 1 is provided with a mold 2 having a through hole and capable of being heated, and an upper pin 4 and a lower pin 6 capable of moving up and down in the through hole of the mold 2, and it is possible to produce the molded article by introducing the protein composition into a space created by inserting the upper pin 4 or the lower pin 6 into the mold 2 and compressing the composition with the upper pin 4 and the lower pin 6 while heating the mold 2.

Figure 2:
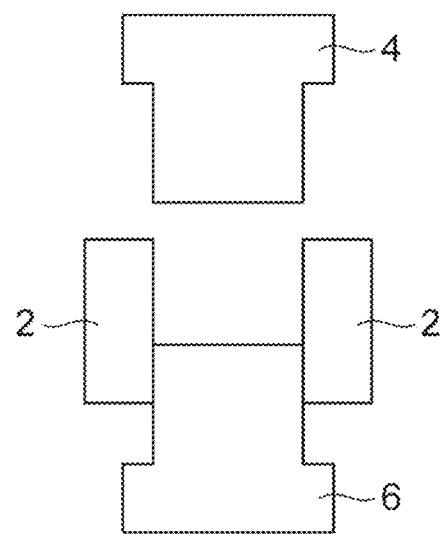
FIG. 2 illustrates schematic cross-sectional views of the press molding machine (a) before the introduction of a composition, (b) immediately after the introduction of the composition, and (c) with the composition in a state of being hot pressed.
Figure 2:
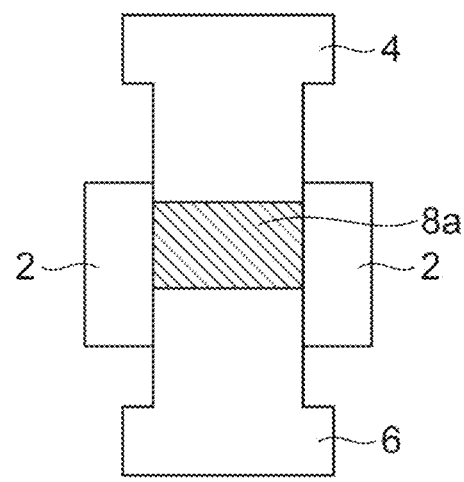
Figure 2:
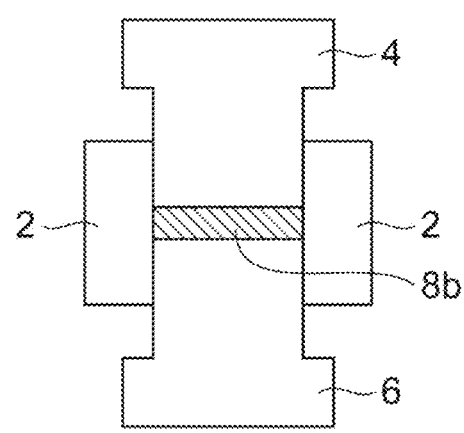

As illustrated in FIG. 2(a), the protein composition is introduced into the through hole in a state in which only the lower side pin 6 is inserted into the through hole of the die 2, and, as illustrated in FIG. 2(b), the upper side pin 4 is inserted into the through hole of the die 2 and moved down, and the heating of the die 2 is initiated, thereby heating and pressing a protein composition 8a which is not yet heated and pressed in the through hole. The upper side pin 4 is moved down until a predetermined pressurization force is reached, and heating and pressing are continued until the protein composition reaches a predetermined temperature in a state illustrated by FIG. 2(c), thereby obtaining a protein composition 8b which has been hot pressed. After that, the temperature of the die 2 is lowered using a cooler (for example, a spot cooler), the upper side pin 4 or the lower side pin 6 is removed from the die 2 when the protein composition 8b reaches a predetermined temperature, and the resulting content is taken out, thereby obtaining a molded article. The pressing may be carried out by moving down the upper side pin 4 in a state in which the lower side pin 6 is fixed, but it is also possible to move down the upper side pin 4 and move up the lower side pin 6 at the same time.

The heating is preferably carried out at 80° C. to 300° C., more preferably carried out at 100° C. to 200° C., and still more preferably carried out at 130° C. to 200° C. The pressing is preferably carried out at 5 kN or more, more preferably carried out at 10 kN or more, and still more preferably carried out at 20 kN or more. In addition, the time during which the treatment is continued under predetermined hot pressing conditions after the conditions are satisfied (temperature retention condition) is preferably 0 to 100 minutes, more preferably 1 to 50 minutes, and still more preferably 5 to 30 minutes.

When the protein composition according to the first embodiment contains propyl 3,4,5-trihydroxybenzoate or 6,6'-di-tert-butyl-4,4'-butylidenedi-m-cresol as a stabilizer, the dry matter of the protein composition (for example, a molded article) has superior bending strength.

The protein composition (protein composition 2) according to the second embodiment is a protein composition containing dry matter of a solution in which a protein and a stabilizer are dissolved, in which the stabilizer includes at least one type selected from the group consisting of N,N'-hexane-1,6-diyl bis[3-(3,5-di-tert-butyl-4-hydroxyphenyl) propionamide], 1,6-hexanediol bis[3-(3,5-di-tert-butyl-4-hydroxyphenyl)propionate], 6,6'-di-tert-butyl-4,4'-butylidene di-m-cresol, 2,6-di-tert-butyl-p-cresol, 3,9-bis(2,6-di-tert-butyl-4-methylphenoxy)-2,4,8,10-tetraoxa-3,9-diphosphaspiro[5.5]undecane, poly[[6-[(1,1,3,3-tetramethylbutyl)amino]-1,3,5-triazine-2,4-diyl][(2,2,6,6-tetramethyl-4-piperidinyl)imino]-1,6-hexanediyl[(2,2,6,6-tetramethyl-4-piperidinyl)imino]], α-tocopherol, propyl 3,4,5-trihydroxybenzoate, and 4,4',4"-(1-methylpropanyl-3-ylidene) tris(6-tert-butyl-m-cresol). Below, these stabilizers are referred to as "stabilizers for the second embodiment".

A preferable second embodiment stabilizer is preferably
a combination of propyl 3,4,5-trihydroxybenzoate and 2,2'-methylene bis(4,6-di-tert-butylphenyl)2-ethylhexyl phosphite, a combination of 6,6'-di-tert-butyl-4,4'-butylidene di-m-cresol and thiobis[2-(1,1-dimethylethyl)-5-methyl-4,1-phenylene]-bis[3-(dodecylthio)propionate],
a combination of N,N'-hexane-1,6-diyl bis(3-(3,5-di-tert-butyl-4-hydroxyphenylpropionamide)) and 2,2'-methylene bis(4,6-di-tert-butylphenyl)2-ethylhexyl phosphite, a combination of poly[[6-[(1,1,3,3-tetramethylbutyl) amino]-1,3,5-triazine-2,4-diyl][(2,2,6,6-tetramethyl-4-piperidinyl)imino]-1,6-hexanediyl[(2,2,6,6-tetramethyl-4-piperidinyl)imino]] and 3,9-bis(2,6-di-tert-butyl-4-methylphenoxy)-2,4,8,10-tetraoxa-3,9-diphosphaspiro[5.5] undecane,
a combination of poly[[6-[(1,1,3,3-tetramethylbutyl) amino]-1,3,5-triazine-2,4-diyl][(2,2,6,6-tetramethyl-4-piperidinyl)imino]-1,6-hexanediyl[(2,2,6,6-tetramethyl-4-piperidinyl)imino]] and 2,2'-methylene bis(4,6-di-tert-butylphenyl)2-ethylhexyl phosphite, or
a combination of poly[[6-[(1,3,3,-tetramethylbutyl) amino]-1,3,5-triazine-2,4-diyl][(2,2,6,6-tetramethyl-4-piperidinyl)imino]-1,6-hexanediyl[(2,2,6,6-tetramethyl-4-piperidinyl)imino]] and thiobis[2-(1,1-dimethylethyl)-5-methyl-4,1-phenylene]-bis[3-(dodecylthio)propionate].

When the stabilizer is any of the above combinations, the heat stability of the protein composition containing the above is further improved.

In the protein composition 2, the content of the stabilizer with respect to 100 parts by mass of protein is preferably more than 0 parts by mass and 10 parts by mass or less, more preferably 0.001 parts by mass or more and 10 parts by mass or less, even more preferably 0.01 parts by mass or more and 5 parts by mass or less, still more preferably 0.1 parts by mass or more and 2 parts by mass or less, yet more preferably 0.1 parts by mass or more and 1 part by mass or less, and yet more preferably 0.1 parts by mass or more and 0.5 parts by mass or less. This is because, even if the content is increased to more than 10 parts by mass, the corresponding improvement in heat stability is reduced. It is possible to produce the protein composition 2 using, for example, a production method provided with a step of obtaining a mixed solution by mixing a protein, a solution for dissolving the protein, and a stabilizer solution, and a step of obtaining dry matter by removing volatile components from the mixed solution (the production method 2 described above). In addition, the protein composition 2 may be a composition in which dry matter is dissolved in a solvent or the like.

The protein composition 2 may be formed only of the dry matter described above or may contain other components. That is, the protein composition 2 may contain other components than the protein and the stabilizer. In addition, when the protein composition 2 is obtained, other components may be dissolved in the solvent.

The solvent for dissolving the protein may be any solvent able to dissolve the protein, and examples thereof include a mixed solvent of calcium chloride/ethanol/water, DMSO, HFIP, formic acid, and the like. The addition amount of the dissolving solvent is an amount able to dissolve the protein, and for example, it is preferable to adjust the amount of the protein to be 10 to 24% by mass.

Examples of the solvent for producing a solution of the stabilizer for the second embodiment include single solvents such as primary alcohols (e.g. ethanol and methanol), secondary alcohols (e.g. 2-propanol), tertiary alcohols (e.g. tert-butyl alcohol), acetone, methyl ethyl ketone, or dichloromethane, mixed solvents of at least two of these solvents, and the like. The upper limit of the concentration of the stabilizer for the second embodiment is the solubility of the stabilizer with respect to the solvent for dissolving the protein.

In order to obtain a mixed solution, the protein is preferably in powder form. In addition, it is preferable to produce a mixed solution according to the preferable ratios described above of the protein and the stabilizer for the second embodiment. The mixed solution may be prepared, for example, by mixing a protein, a solvent for dissolving protein, and the stabilizer for the second embodiment, and stirring at 65° C.±5° C. for 3 to 6 hours. Both the protein and the stabilizer for the second embodiment are dissolved in the mixed solution (dope solution) obtained in this manner.

The dry matter of the protein composition 2 is typically not in powder form (film form, fiber form, string form, plate form, and the like). The dry matter of the protein composition 2 may be an article (film, plate, fiber, string, or the like). For example, the mixed solution (dope solution) obtained as described above is cast on a substrate made of polystyrene and dried under reduced pressure (for example, at 60° C., 0.54 atm for 7 days) to carry out molding. After that, the result is immersed in acetone/methanol mixed solution (ratio 7:3) for 30 minutes, further immersed in a methanol solution for 30 minutes, and then allowed to dry naturally (for example, at 25° C., 1 atm) to make it possible to obtain the dry matter (film form or plate form) of the protein composition 2. In addition, spinning the mixed solution (dope solution) obtained as described above makes it possible to obtain the dry matter (fiber form or string form) of the protein composition 2.

Carrying out the production methods 1 and 2 described above makes it possible for this protein and the stabilizer to both be present and, due to this, it is possible to improve the heat stability of the protein. That is, a heat stability improving method (method 1 described above), in which a dispersion is obtained by dispersing the protein in a solution in which the stabilizer for the first embodiment is dissolved, and dry matter in which both the protein and the compound are present is obtained by removing volatile components from the dispersion, and a heat stability improving method (method 2 described above), in which a mixed solution is obtained by mixing a protein, a solvent for dissolving the protein, and a solution of the stabilizer for the second embodiment, and dry matter in which both the protein and the compound are present is obtained by removing volatile components from the mixed solution, are provided.

It is possible to carry out a method for evaluating the heat stability of the protein compositions 1 and 2 using a commonly used method. Examples thereof include a chemiluminescence method, thermogravimetry/differential heat analysis simultaneous measurement (TG-DTA), differential scanning calorimetry (DSC), high pressure differential scanning calorimetry (HP-DSC), accelerating rate calorimetry (ARC), or various methods such as mechanical testing such as tensile testing, bending testing (for example, flexural strength testing), compression testing, and impact testing.

The chemiluminescence method is an analysis method for evaluating deterioration by detecting weak chemiluminescence caused by thermal oxidation deterioration. Chemiluminescence is the light produced by the return of molecules from an excited state to a ground state during chemical reactions between substances, and the chemiluminescence in polymer deterioration is said to occur when excited carbonyl produced by auto-oxidative deterioration falls into a ground state. In a case of an olefin-based polymer compound such as polypropylene with a stabilizer introduced therein, there is almost no light emission from the material while the stabilizer exhibits an effect, but, when the stabilizer is consumed, chemiluminescence is observed due to the rapid progress of auto-oxidative deterioration. In this manner, the time until the effect of the stabilizer is lost and light is emitted is called the oxidation induction time (OIT), and this time is an indicator which shows the stability of the substance.

On the other hand, some non-olefin-based polymer compounds such as polyamide 6 have no OIT and exhibit behaviors such as the emission intensity gradually increasing when heated and decreasing after exhibiting a maximum value. In a case where such a material is stabilized, since a decrease in the emission intensity and a delay in the time until the maximum value (Extension of Tune at $I_{max}$ [%]) are observed, it is possible to regard these as indicators of stability.

The type of protein is not particularly limited either in the first embodiment or in the second embodiment. The protein may be a protein produced by a microorganism or the like using genetic recombination techniques, may be a protein produced synthetically, or may be a protein obtained by refining a protein of natural origin.

The protein may, for example, be a structural protein. A structural protein means a protein which forms or maintains a structure, a form, or the like in vivo. Examples of such structural proteins include fibroin, collagen, elastin, resilin, and the like. These proteins are used alone or in combination as appropriate as structural proteins.

The fibroin may be, for example, one type or more selected from the group consisting of silk fibroin, spider silk fibroin, and hornet silk fibroin. In particular, the structural protein may be silk fibroin, spider silk fibroin, or a combination thereof. In a case where silk fibroin and spider silk fibroin are used in combination, the ratio of silk fibroin may be, for example, 40 parts by mass or less, 30 parts by mass or less, or 10 parts by mass or less with respect to 100 parts by mass of spider silk fibroin.

Silk yarn is a fiber (cocoon filament) obtained from cocoons made by silkworms, which are the larvae of silkworm moths (*Bombyx mori*). Generally, one cocoon filament is formed of two silk fibroins and a gluey substance (sericin) covering the fibroins from the outside. Silk fibroins are formed of a large number of fibrils. Silk fibroins are covered with four layers of sericin. In practice, silk filaments obtained by dissolving and removing the sericin on the outside by refining are used in clothing applications. Typical silk yarn has a specific gravity of 1.33, a fineness of 3.3 decitex on average, and a fiber length of approximately 1300 to 1500 m. It is possible to obtain silk fibroin as a raw material from natural or domestic silkworm cocoons, or used or discarded silk fabrics.

The silk fibroin may be sericin-removed silk fibroin, sericin-unremoved silk fibroin, or a combination thereof. The sericin-removed silk fibroin is refined by removing the sericin covering the silk fibroin, other fats, and the like. The silk fibroin refined in this manner is preferably used as a lyophilized powder. Sericin-unremoved silk fibroin is unrefined silk fibroin from which sericin and the like are not removed.

The spider silk fibroin may contain a spider silk polypeptide selected from the group consisting of natural spider silk proteins and polypeptides derived from natural spider silk proteins.

Examples of natural spider silk proteins include major dragline silk proteins, flagelliform silk proteins, and tubuliform proteins. The major dragline silk has repeating regions formed of a crystalline region and a non-crystalline region (amorphous region) and thus has both high stress and elasticity. The flagelliform spider silk has a characteristic of having repeating regions formed of amorphous regions without having a crystalline region. The flagelliform spider silk is inferior in stress as compared with the major dragline silk, but has high elasticity.

The major dragline silk protein is produced in the ampullate gland and has a characteristic of having excellent toughness. Examples of major dragline silk proteins include the major ampullate spidroins MaSp1 and MaSp2 derived from American silk spiders (*Nephila clavipes*) and ADF3 and ADF4 derived from European garden spiders (*Araneus diadematus*). ADF3 is one of the two major dragline proteins of European garden spiders. The polypeptides derived from natural spider silk proteins may be polypeptides derived from these dragline proteins. The polypeptide derived from ADF3 is relatively easy to synthesize, and has excellent characteristics in terms of strength-elongation degree and toughness.

The flagelliform silk protein is produced in the flagelliform gland of the spider. Examples of flagelliform silk proteins include flagelliform silk protein derived from American silk spiders (*Nephila clavipes*).

The polypeptide derived from a natural spider silk protein may be a recombinant spider silk protein. Examples of recombinant spider silk proteins include mutations, analogues, derivatives, or the like of natural spider silk proteins. A preferable example of such a polypeptide is a recombinant spider silk protein of a major dragline silk protein (also referred to as "a polypeptide derived from a major dragline silk protein").

Examples of proteins derived from the major dragline silk or proteins derived from silkworm silk, which are fibroin proteins, include a protein including a domain sequence represented by Formula 1: $[(A)_n \text{ motif-REP1}]_m$ (here, in Formula 1, the $(A)_n$ motif indicates an amino acid sequence formed of 4 to 20 amino acid residues, and the number of alanine residues with respect to the total number of amino acid residues in the $(A)_n$ motif is 80% or more. REP1 indicates an amino acid sequence formed of 10 to 200 amino acid residues. m represents an integer of 8 to 300. The plurality of present $(A)_n$ motifs may be amino acid sequences which are identical to each other or amino acid sequences which are different from each other. The plurality of present REP1 may be amino acid sequences which are identical to each other or amino acid sequences which are different from each other.) Specific examples thereof include a protein including the amino acid sequence shown in SEQ ID No. 1.

Examples of a protein derived from the flagelliform silk protein include a protein including a domain sequence represented by Formula 2: $[\text{REP2}]_o$ (here, in Formula 2, REP2 indicates an amino acid sequence formed from Gly-Pro-Gly-Gly-X, and X indicates one amino acid selected from the group consisting of alanine (Ala), serine (Ser), tyrosine (Tyr), and valine (Val). o represents an integer of 8 to 300.) Specific examples thereof include a protein including the amino acid sequence shown in SEQ ID No. 2. The amino acid sequence shown in SEQ ID No. 2 is a sequence in which an amino acid sequence (denoted as PR1 sequence) from residue 1220 to residue 1659 from the N-terminus corresponding to the repeat portion and motif of a partial sequence (NCBI accession number: AAF36090, GI: 7106224) of the flagelliform silk protein of the American silk spider obtained from the NCBI database is linked with a C-terminus amino acid sequence from residue 816 to residue 907 from the C-terminus of the partial sequence (NCBI accession numbers: AAC38847, GI: 2833649) of the flagelliform silk protein of the American silk spider obtained from the NCBI database, and the amino acid sequence (tag sequence and hinge sequence) shown in SEQ ID No. 6 is added to the N-terminus of the linked sequence.

Examples of a protein derived from collagen include a protein including a domain sequence represented by Formula 3: $[\text{REP3}]_p$ (here, in Formula 3, p represents an integer of 5 to 300. REP3 represents an amino acid sequence composed of Gly-X-Y and X and Y represent arbitrary amino acid residues other than Gly. The plurality of REP3 may be amino acid sequences which are identical to each other or amino acid sequences which are different from each other.) Specific examples thereof include a protein including the amino acid sequence shown in SEQ ID No. 3. The amino acid sequence shown in SEQ ID No. 3 is a sequence in which the amino acid sequence (tag sequence and hinge sequence) shown in SEQ ID No. 6 is added to the N-terminus of the amino acid sequence from residue 301 to residue 540 corresponding to the repeat portion and motif of a partial sequence (NCBI Genbank accession numbers: CAA56335.1, GI: 3702452) of human collagen type 4 obtained from the NCBI database.

Examples of a protein derived from resilin include a protein including a domain sequence represented by Formula 4: $[\text{REP4}]_q$ (here, in Formula 4, q indicates an integer of 4 to 300. REP4 indicates an amino acid sequence formed of Ser-J-J-Tyr-Gly-U-Pro. J indicates an arbitrary amino acid residue, and is particularly preferably an amino acid residue selected from the group consisting of Asp, Ser, and Thr. U indicates an arbitrary amino acid residue, and is particularly preferably an amino acid residue selected from the group consisting of Pro, Ala, Thr, and Ser. The plurality of present REP4 may be amino acid sequences which are identical to each other or amino acid sequences which are different from each other.) Specific examples thereof include a protein including the amino acid sequence shown in SEQ ID No. 4. The amino acid sequence shown in SEQ ID No. 4 is a sequence in which, in the amino acid sequence of resilin (NCBI Genbank accession numbers NP611157 and GI: 24654243), the amino acid sequence (tag sequence and hinge sequence) shown in SEQ ID No. 6 is added to the N-terminus of the amino acid sequence from residue 19 to residue 321 of a sequence in which Thr of residue 87 is substituted with Ser and Asn of residue 95 is substituted with Asp.

Examples of a protein derived from elastin include a protein having an amino acid sequence such as NCBI Genbank Accession No. AAC98395 (human), I47076 (sheep), and NP786966 (cow). Specific examples thereof include a protein including the amino acid sequence shown in SEQ ID No. 5. The amino acid sequence represented by SEQ ID No. 5 is a sequence in which the amino acid sequence (tag sequence and hinge sequence) represented by SEQ ID No. 6 is added to the N-terminus of the amino acid sequence from residue 121 to residue 390 of the amino acid sequence of NCBI Genbank Accession No. AAC98395.

It is possible to produce a protein included as a main component in a protein raw material fiber, for example, by using a host genetically transformed with an expression vector having a nucleic acid sequence encoding the protein and one or a plurality of regulatory sequences operably linked to the nucleic acid sequence in order to express the nucleic acid.

The method for producing a gene encoding the protein included as a main component in the protein raw material fiber is not particularly limited. For example, it is possible to produce a gene using a method of amplification and cloning by a polymerase chain reaction (PCR) or the like, using a gene encoding a natural structural protein, or by chemical synthesis. The chemical synthesis method of the gene is not particularly limited, and, for example, it is possible to chemically synthesize the gene by a method of linking automatically synthesized oligonucleotides by PCR or the like in an AKTA oligopilot plus 10/100 (GE Healthcare Japan Co., Ltd.), or the like based on the amino acid sequence information of the structural protein obtained from the NCBI web database or the like. At this time, in order to facilitate the refining or confirmation of protein, a gene encoding a protein made of an amino-acid sequence obtained by adding an amino-acid sequence made up of a start codon and a His10 tag to an N terminal of the amino-acid sequence may be synthesized.

A regulatory sequence is a sequence which controls the expression of a recombinant protein in a host (for example, a promoter, an enhancer, a ribosome binding sequence, a transcription termination sequence, and the like), and it is possible to appropriately select the regulatory sequence depending on the type of host. As a promoter, an inducible promoter may be used which functions in host cells and is capable of inducing the expression of a target protein. An inducible promoter is a promoter which is able to control the transcription due to physical factors such as the presence of an inducer (expression inducer), the absence of a repressor molecule, or an increase or decrease in the temperature, osmotic pressure, or pH value.

It is possible to appropriately select the type of expression vector according to the type of host, such as a plasmid vector, a viral vector, a cosmid vector, a fosmid vector, and an artificial chromosome vector. As the expression vector, it is preferable to use a vector capable of autonomous replication in a host cell or capable of integration into a host chromosome and containing a promoter at a position at which it is possible to carry out transcription of the nucleic acid encoding the target protein.

As a host, it is possible to suitably use any of prokaryotes or eukaryotes such as yeast, filamentous fungi, insect cells, animal cells, and plant cells.

Preferable examples of prokaryotes include bacteria belonging to *Escherichia, Brevibacillus, Serratia, Bacillus, Microbacterium, Brevibacterium, Corynebacterium, Pseudomonas*, and the like. Examples of microorganisms belonging to *Escherichia* include *Escherichia coli* and the like. Examples of microorganisms belonging to *Brevibacillus* include *Brevibacillus agri* and the like. Examples of microorganisms belonging to *Serratia* include *Serratia liquofaciens* and the like. Examples of microorganisms belonging to *Bacillus* include *Bacillus subtilis* and the like. Examples of microorganisms belonging to *Microbacterium* include *Microbacterium ammoniafilum* and the like. Examples of microorganisms belonging to *Brevibacterium* include *Brevibacterium divaricatam* and the like. Examples of microorganisms belonging to *Corynebacterium* include *Corynebacterium ammoniagenes* and the like. Examples of microorganisms belonging to *Pseudomonas* include *Pseudomonas putida* and the like.

Examples of vectors for introducing a nucleic acid encoding a protein included in the protein raw material fiber as a main component include pBTrp2 (manufactured by Boehringer Mannheim), pGEX (manufactured by Pharmacia), pUC18, pBluescript II, pSupex, pET22b, pCold, pUB110, pNCO2 (Patent Literature: JP 2002-238569 A), and the like.

Examples of eukaryotic hosts include yeast and filamentous fungi (molds and the like). Examples of yeast include yeast belonging to *Saccharomyces, Pichia, Schizosaccharomyces*, and the like. Examples of filamentous fungi include filamentous fungi belonging to *Aspergillus, Penicillium, Trichoderma*, and the like.

Examples of vectors include YEp13 (ATCC 37115), YEp24 (ATCC 37051), and the like. As a method of introducing an expression vector into the host cell, it is possible to use any method of introducing DNA into a host cell. Examples thereof include a method using calcium ions [Proc. Natl. Acad. Sci. USA, 69, 2110 (1972)], an electroporation method, a spheroplast method, a protoplast method, a lithium acetate method, a competent method, and the like.

As a method of expressing a nucleic acid using a host genetically transformed with an expression vector, in addition to direct expression, it is possible to carry out secretory production, fusion protein expression, and the like according to the method described in Molecular Cloning Second Edition, or the like.

It is possible to produce a protein, for example, by culturing a host genetically transformed with an expression vector in a culture medium, producing and accumulating the protein in the culture medium, and collecting the protein from the culture medium. It is possible to perform the method of culturing the host in a culture medium in accordance with a method typically used for culturing a host.

In a case where the host is a prokaryote such as *Escherichia coli* or a eukaryote such as yeast, either a natural medium or a synthetic medium may be used as the culture medium as long as a carbon source which is able to be utilized by the host, a nitrogen source, inorganic salts, and the like are contained therein and the medium is able to efficiently culture the host.

The carbon source may be any source as long as the genetically transformed microorganism described above is able to utilize the source, and it is possible to use, for example, glucose, fructose, sucrose, and molasses containing these, carbohydrates such as starch and starch hydrolysate, organic acids such as acetic acid and propionic acid, and alcohols such as ethanol and propanol. As nitrogen sources it is possible to use, for example, ammonium salts of inorganic acids or organic acids such as ammonia, ammonium chloride, ammonium sulfate, ammonium acetate, and ammonium phosphate, other nitrogen-containing compounds, peptone, meat extract, yeast extract, corn steep liquor, casein hydrolyzate, soybean meal, and soybean meal hydrolyzate, various fermented bacterial cells, and digests thereof. As the inorganic salt, for example, it is possible to use potassium phosphate, dipotassium phosphate, magnesium phosphate, magnesium sulfate, sodium chloride, ferrous sulfate, manganese sulfate, copper sulfate, and calcium carbonate.

It is possible to perform culturing of a prokaryote such as *Escherichia coli* or a eukaryote such as yeast under aerobic conditions, such as shaking culturing or submerged aeration stirring culturing. The culturing temperature is, for example, 15 to 40° C. The culturing time is usually 16 hours to 7 days. The pH of the culture medium during culturing is preferably maintained at 3.0 to 9.0. It is possible to adjust the pH of the culture medium using an inorganic acid, an organic acid, an alkali solution, urea, calcium carbonate, ammonia, or the like.

In addition, antibiotics such as ampicillin and tetracycline may be added to the culture medium as necessary during culturing. When a microorganism genetically transformed with an expression vector using an inducible promoter as a promoter is cultured, an inducer may be added to the medium as necessary. For example, when culturing a microorganism genetically transformed with an expression vector using a lac promoter, isopropyl β-D-thiogalactopyranoside, or the like may be added to the medium, and, when culturing a microorganism genetically transformed with an expression vector using a trp promoter, an indole acrylic acid or the like may be added to the medium.

It is possible to carry out protein isolation and refining by a commonly used method. For example, in a case where the protein is expressed in a dissolved state in cells, after completion of the culturing, host cells are recovered by centrifugation and suspended in an aqueous buffer solution, then the host cells are crushed by an ultrasonic crusher, a French press, a Manton Gaulin homogenizer, a dynomill, or the like and a cell-free extract is obtained. It is possible to use a method usually used for isolation and refining of proteins from a supernatant obtained by centrifuging a cell-free extract, that is, a solvent extraction method, a salting out method using ammonium sulfate or the like, a desalting method, a precipitation method using organic solvent, an anion exchange chromatography method using a resin such as diethylaminoethyl (DEAE)-sepharose, or DIAION HPA-75 (manufactured by Mitsubishi Chemical Co., Ltd.), a cation exchange chromatography method using a resin such as S-Sepharose FF (manufactured by Pharmacia), a hydrophobic chromatography method using a resin such as butyl sepharose or phenyl sepharose, a gel filtration method using a molecular sieve, an affinity chromatography method, a chromatofocusing method, or a method such as an electrophoresis method such as an isoelectric point electrophoresis method, as a single method or in a combination of methods to obtain a refined preparation.

In addition, in a case where the protein is expressed by forming an insoluble form in the cells, the host cells are recovered in the same manner, and then crushed and centrifuged to recover the insoluble form of the modified fibroin as a precipitated fraction. It is possible to solubilize the insoluble form of the recovered modified fibroin with a protein denaturant. After this operation, it is possible to obtain a refined preparation of modified fibroin by the same isolation and refining method as described above. In a case where the protein is secreted outside the cells, it is possible to recover the protein from a culture superatant. That is, it is possible to obtain a refined preparation by acquiring a culture supernatant by treating the culture by a method such as centrifugation and using the same isolation and refining methods as described above on the culture supernatant.

In addition, the protein raw material fiber which includes protein as described above as a main component is produced by a well-known method. That is, for example, when producing a protein raw material fiber including spider silk fibroin, first, spider silk fibroin produced using a host or the like genetically transformed with the expression vector is dissolved in a single solvent such as dimethyl sulfoxide (DMSO), N,N-dimethyl formamide (DMF), formic acid, or hexafluoroisopropanol (HFIP) to produce a dope solution, or the spider silk fibroin described above is added together with an inorganic salt as a dissolution accelerator to these solvents and dissolved to produce a dope solution. Next, using this dope solution, it is possible to obtain the protein raw material by spinning using a known spinning method such as wet spinning, dry spinning, dry and wet spinning, or the like. In addition, a stabilizer may be added to the dope solution described above and dissolved, and, in addition, the spider silk fibroin described above may be mixed with a solution in which the stabilizer is dissolved to prepare a dope solution. Here, as a solvent for the dope solution to be used, a solvent capable of dissolving the stabilizer may also be used. A mixed solution of a solution in which the stabilizer is dissolved and a solution in which the spider silk fibroin is dissolved may be used as the dope solution.

Furthermore, the spider silk fibroin may be dispersed in a solution in which a stabilizer is dissolved to obtain a dispersion, and dry matter obtained by removing the solvent from the dispersion may be used to produce a dope solution.

EXAMPLES

A more specific description will be given below of the present invention based on Examples. However, the present invention is not limited to the following Examples.

1. Production of Spider Silk Protein (Spider Silk Fibroin)

(Synthesis of Gene Encoding Spider Silk Protein and Construction of Expression Vector)

Based on the base sequence and amino acid sequence of fibroin (GenBank accession number. P46804.1, GI: 1174415) derived from *Nephila clavipes*, a modified fibroin having the amino acid sequence shown in SEQ ID No. 1 (may also be referred to as "PRT410") was designed.

The amino acid sequence shown in SEQ ID No. 1 has an amino acid sequence obtained by substituting, inserting, and deleting amino acid residues with respect to the amino acid sequence of fibroin derived from *Nephila clavipes* for the purpose of improving productivity, and the amino acid sequence (tag sequence and hinge sequence) shown in SEQ ID No. 6 is added to the N-terminus thereof.

Next, the nucleic acid encoding PRT410 was synthesized. The NdeI site at the 5' terminus and the EcoRI site downstream of the stop codon were added to the nucleic acid. The nucleic acid was cloned into a cloning vector (pUC118). Thereafter, the same nucleic acid was subjected to a restriction enzyme treatment with NdeI and EcoRI, cut out, and then recombined into a protein expression vector pET-22b (+) to obtain an expression vector.

*Escherichia coli* BLR (DE3) was genetically transformed with the pET22b(+) expression vector including a nucleic acid encoding a protein having the amino acid sequence shown in SEQ ID No. 1. The genetically transformed *Escherichia coli* was cultured in 2 mL of LB medium including ampicillin for 15 hours. The culture solution was added to 100 mL of a seed culture (Table 1) including ampicillin such that the $OD_{600}$ was 0.005. The culture solution temperature was maintained at 30° C., and flask culturing was performed until the $OD_{600}$ reached 5 (approximately 15 hours) to obtain a seed culture solution.

TABLE 1

| Reagent | Concentration (g/L) |
| --- | --- |
| Glucose | 5.0 |
| $KH_2PO_4$ | 4.0 |
| $K_2HPO_4$ | 9.3 |
| Yeast Extract | 6.0 |
| Ampicillin | 0.1 |

The seed culture solution was added to a jar fermenter to which 500 mL of a production medium (Table 2 below) was added such that the $OD_{600}$ was 0.05. Culturing was carried out by maintaining the temperature of the culture solution at 37° C., and constantly controlling the pH to be 6.9. In addition, the dissolved oxygen concentration in the culture solution was maintained at 20% of the dissolved oxygen saturation concentration.

TABLE 2

| Reagent | Concentration (g/L) |
| --- | --- |
| Glucose | 12.0 |
| $KH_2PO_4$ | 9.0 |
| $MgSO_4 \cdot 7H_2O$ | 2.4 |
| Yeast Extract | 15 |
| $FeSO_4 \cdot 7H_2O$ | 0.04 |
| $MnSO_4 \cdot 5H_2O$ | 0.04 |
| $CaCl_2 \cdot 2H_2O$ | 0.04 |
| ADEKA NOL (Adeka, LG-295S) | 0.1(mL/L) |

Immediately after the glucose in the production medium was completely consumed, a feed solution (glucose 455 g/l L, Yeast Extract 120 g/l L) was added at a rate of 1 mL/min. Culturing was carried out by maintaining the temperature of the culture solution at 37° C., and constantly controlling the pH to be 6.9. In addition, the culturing was performed for 20 hours such that the dissolved oxygen concentration in the culture solution was maintained at 20% of the dissolved oxygen saturation concentration. Thereafter, 1 M isopropyl β-thiogalactopyranoside (IPTG) was added to the culture solution to have a final concentration of 1 mM and the target protein was expressed and induced. Twenty hours after the addition of IPTG, the culture solution was centrifuged and bacterial cells were recovered. SDS-PAGE was performed using bacterial cells prepared from the culture solution before and after IPTG addition, and expression of the target protein was confirmed according to the appearance of a band of the target protein size depending on the IPTG addition.

(Protein Refining)

Two hours after the addition of IPTG, the recovered bacterial cells were washed with a 20 mM Tris-HCl buffer (pH 7.4). The washed bacterial cells were suspended in a 20 mM Tris-HCl buffer (pH 7.4) including approximately 1 mM of PMSF, and the cells were crushed in a high-pressure homogenizer (GEA Niro Soavi). The crushed cells were centrifuged to obtain a precipitate. The obtained precipitate was washed with a 20 mM Tris-HCl buffer (pH 7.4) to have a high purity. The washed precipitate was suspended in 8 M guanidine buffer (8 M guanidine hydrochloride, 10 mM sodium dihydrogen phosphate, 20 mM NaCl, 1 mM Tris-HCl, pH 7.0) to have a concentration of 100 mg/mL, and stirred with a stirrer for 30 minutes at 60° C. to dissolve. After dissolution, dialysis was performed with water using a dialysis tube (a cellulose tube 36/32, manufactured by Sanko Junyaku Co., Ltd.). The white aggregated protein obtained after the dialysis was recovered by centrifugation, the water was removed by a lyophilizer machine, and lyophilized powder was recovered.

The degree of refining of the target protein in the obtained lyophilized powder was confirmed by image analysis of the result of polyacrylamide gel electrophoresis of the powder using TotalLab (Nonlinear Dynamics Ltd.). As a result, the degree of refining of both proteins was approximately 85%.

2-1. Production of Protein Composition 1 (Powder)

200 mg of artificial spider silk protein powder obtained in the above refining step was introduced into various sample bottles. The stabilizers shown in Table 3 below were dissolved in a solvent (a mixed solvent of acetone/methanol at a volume ratio of 1/1) at a concentration of 0.3 mg/mL, and 2 mL of the stabilizer solution was introduced into each sample bottle (Stabilizer amount: 0.6 mg). The sample bottles were sealed and stirred at room temperature for 16 hours, and then naturally dried to evaporate the solvent and prepare a stabilizer-containing powder (powder-form protein composition) (stabilizer content with respect to total amount of dry matter: 0.3% by mass).

A protein powder was prepared in the same manner as described above, except that no stabilizer was added, and used as a control.

TABLE 3

| Stabilizer Name |
| --- |
| 2-(3,4-dihydroxyphenyl)-3,5,7-trihydroxy-4H-chromen-4-one |
| (1S,3R,4R,5R)-3-{[3-(3,4-dihydroxyphenyl)acryloyl]oxy}-1,4,5-trihydroxycyclohexane-1-carboxylic acid |
| 2-(3,4-dihydroxyphenyl)-5,7-dihydroxy-3-{[(2S,3R,4S,5S,6R)-3,4,5-trihydroxy-6-({[(2R,3R,4R,5R,6S)-3,4,5-trihydroxy-6-methyloxan-2-yl]oxy}methyl)oxan-2-yl]oxy}-4H-chromen-4-one |
| Propyl 3,4,5-trihydroxybenzoate |
| 4,4'-(2,3-dimethylbutane-1,4-diyl)dibenzene-1,2-diol |
| 6-hydroxy-2,5,7,8-tetramethylchroman-2-carboxylic acid |
| 2,6-di-tert-butyl-p-cresol |
| 2-tert-butyl-4-methoxyphenol |
| Probucol |
| Octadecyl 3-(3,5-di-tert-butyl-4-hydroxyphenyl)propionate |
| Hexamethylene bis[3-(3,5-di-tert-butyl-4-hydroxyphenyl)propionate] |
| Dilauryl 3,3'-thiodipropionate |
| 2,2',6,6'-tetra-tert-butyl-[1,1'-biphenyl]-4,4'-diol |
| 3-methyl-1-phenyl-5-pyrazolone |
| 3,4-methylenedioxyphenol |
| 2,2',6,6'-tetra-tert-butyl-4,4'-dihydroxybiphenyl |
| 4,4',4''-(1-methylpropanyl-3-ylidene)tris(6-tert-butyl-m-cresol) |
| 3-[3-(3,5-di-tert-butyl-4-hydroxyphenyl)propanoyloxy]-2,2-bis[3-(3,5-di-tert-butyl-4-hydroxyphenyl)propanoyloxymethyl]propyl 3-(3,5-di-tert-butyl-4-hydroxyphenyl)propanoate |
| Tris(2,4-di-tert-butylphenyl) phosphite |
| 2,2-bis{[3-(dodecylthio)-1-oxopropoxy]methyl}propane-1,3-diyl bis[3-(dodecylthio)propionate] |
| 3,9-bis(2,6-di-tert-butyl-4-methylphenoxy)-2,4,8,10-tetraoxa-3,9-diphosphaspiro[5,5]undecane |
| Hesperidin |
| Di(tridecyl) 3,3'-thiodipropionate |
| 3-(4-hydroxyphenyl)-1-(2,4,6-trihydroxyphenyl)-1-propanone |
| N,N'-bis[3-(3,5-di-tert-butyl-4-hydroxyphenyl)propionyl]hydrazine |
| Thiobis[2-(1,1-dimethylethyl)-5-methyl-4,1-phenylene]-bis[3-(dodecylthio)propionate] |
| 1,3,5-tris(3,5-di-tert-butyl-4-hydroxybenzyl)-1,3,5-triazine-2,4,6(1H,3H,5H)-trione |
| 3,9-bis{2-[3-(3-tert-butyl-4-hydroxy-5-methylphenyl)propionyloxy]-1,1-dimethylethyl}-2,4,8,10-tetraoxaspiro[5,5]undecane |
| 2,2'-methylenebis(4,6-ditert-butylphenyl) 2-ethylhexylphosphite |
| 2-(1,1-dimethylethyl)-1,4-benzenediol |
| 2-hydroxy-N-1H-1,2,4-triazol-3-ylbenzamide |
| 4',5-dihydroxystilbene-3-yl β-D-glucopyranoside |
| α-tocopherol |
| 6,6'-di-tert-butyl-4,4'-butylidene di-m-cresol |
| N,N'-hexane-1,6-diyl bis(3-(3,5-di-tert-butyl-4-hydroxyphenylpropionamide)) |
| 1,3,5-tris(3,5-di-tert-butyl-4-hydroxyphenylmethyl)-2,4,6-trimethylbenzene |
| 2-ethylhexyl diphenylphosphite |
| Triethyleneglycol bis(3-tert-butyl-4-hydroxy-5-methylphenyl)propionate |
| N-acetyl-5-methoxytryptamine |
| 2-oxo-L-threo-hexono-1,4-lactone-2,3-enediol |
| 6-ethoxy-1,2-dihydro-2,2,4-trimethylquinoline |

Heat stability evaluation was performed as follows. The stabilizer-containing powder (powder-form protein composition) described above was placed in a chamber for accommodating a sample, and the chamber was set in an apparatus. Thereafter, dry air was circulated at a flow rate of 100 mL/min, maintained at 200° C., and time-dependent changes in chemiluminescence intensity were detected with a chemiluminescence analyzer (CLA-ID2-HS, manufactured by Tohoku Electronic Industrial Co., Ltd.). The time until the chemiluminescence intensity of the protein powder to which the stabilizer was not added reaches a maximum value was set as $T_0$ and the time until the chemiluminescence intensity of the stabilizer-containing powder (powder-form protein composition) reaches the maximum value was set as $T_1$, and the extension of time at $I_{max}$ was calculated from the following equation.

$$(T_1-T_0)/T_0 \times 100 [\%]$$

Extension of Time at $I_{max}$ [%] means the delay time until the chemiluminescence intensity reaches the maximum value, and a larger value indicates a higher heat stability. The results for the stabilizers of Table 3 are shown in Table 4 below.

TABLE 4

| Stabilizer Name | Extension of time at Imax [%] |
|---|---|
| 2-(3,4-dihydroxyphenyl)-3,5,7-trihydroxy-4H-chromen-4-one | 61 |
| (1S,3R,4R,5R)-3-{[3-(3,4-dihydroxyphenyl)acryloyl]oxy}-1,4,5-trihydroxycyclohexane-1-carboxylic acid | 52 |
| 2-(3,4-dihydroxyphenyl)-5,7-dihydroxy-3-{[(2S,3R,4S,5S,6R)-3,4,5-trihydroxy-6-({[(2R,3R,4R,5R,6S)-3,4,5-trihydroxy-6-methyloxan-2-yl]oxy}methyl)oxan-2-yl]oxy}-4H-chromen-4-one | 35 |
| Propyl 3,4,5-trihydroxybenzoate | 28 |
| 4,4'-(2,3-dimethylbutane-1,4-diyl)dibenzene-1,2-diol | 24 |
| 6-hydroxy-2,5,7,8-tetramethylchroman-2-carboxylic acid | 23 |
| 2,6-di-tert-butyl-p-cresol | 23 |
| 2-tert-butyl-4-methoxyphenol | 14 |
| Probucol | 4 |
| Octadecyl 3-(3,5-di-tert-butyl-4-hydroxyphenyl)propionate | 3 |
| Hexamethylene bis[3-(3,5-di-tert-butyl-4-hydroxyphenyl)propionate] | 3 |
| Dilauryl 3,3'-thiodipropionate | 2 |
| 2,2',6,6'-tetra-tert-butyl-[1,1'-biphenyl]-4,4'-diol | 2 |
| 3-methyl-1-phenyl-5-pyrazolone | 2 |
| 3,4-methylenedioxyphenol | 2 |
| 2,2',6,6'-tetra-tert-butyl-4,4'-dihydroxybiphenyl | 2 |
| 4,4'4"-(1-methylpropanyl-3-ylidene) tris(6-tert-butyl-m-cresol) | 1 |
| 3-[3-(3,5-di-tert-butyl-4-hydroxyphenyl)propanoyloxy]-2,2-bis[3-(3,5-di-tert-butyl-4-hydroxyphenyl)propanoyloxy methyl]propyl 3-(3,5-ditert-butyl-4-hydroxyphenyl)propanoate | 1 |
| Tris(2,4-di-tert-butylphenyl) phosphite | 1 |
| 2,2-bis{[3-(dodecylthio)-1-oxopropoxy]methyl}propane-1,3-diyl bis[3-(dodecylthio)propionate] | 1 |
| 3,9-bis(2,6-di-tert-butyl-4-methylphenoxy)-2,4,8,10-tetra oxa-3,9-diphosphaspiro[5,5]undecane | 1 |
| Hesperidin | 1 |
| Di(tridecyl) 3,3'-thiodipropionate | 1 |
| 3-(4-hydroxyphenyl)-1-(2,4,6-trihydroxyphenyl)-1-propanone | 0 |
| N,N'-bis[3-(3,5-di-tert-butyl-4-hydroxyphenyl)propionyl] hydrazine | 0 |
| Thiobis[2-(1,1-dimethylethyl)-5-methyl-4,1-phenylene]-bis[3-(dodecylthio)propionate] | -1 |
| 1,3,5-tris(3,5-di-tert-butyl-4-hydroxybenzyl)-1,3,5-triazine-2,4,6(1H,3H,5H)-trione | -1 |
| 3,9-bis{2-[3-(3-tert-butyl-4-hydroxy-5-methylphenyl)propionyloxy]-1,1-dimethylethyl}-2,4,8,10-tetraoxaspiro[5,5]undecane | -1 |
| 2,2'-methylenebis(4,6-ditert-butylphenyl) 2-ethylhexylphosphite | -1 |
| 2-(1,1-dimethylethyl)-1,4-benzenediol | -2 |
| 2-hydroxy-N-1H-1,2,4-triazol-3-yl benzamide | -3 |
| 4',5-dihydroxystilbene-3-yl β-D-glucopyranoside | -3 |
| α-tocopherol | -3 |
| 6,6'-di-tert-butyl-4,4'-butylidene di-m-cresol | -3 |
| N,N'-hexane-1,6-diyl bis(3-(3,5-di-tert-butyl-4-hydroxyphenylpropionamide)) | -3 |
| 1,3,5-tris(3,5-di-tert-butyl-4-hydroxyphenylmethyl)-2,4,6-trimethylbenzene | -3 |
| 2-ethylhexyl diphenylphosphite | -6 |
| Triethyleneglycol bis(3-tert-butyl-4-hydroxy-5-methylphenyl)propionate | -6 |

TABLE 4-continued

| Stabilizer Name | Extension of time at Imax [%] |
|---|---|
| N-acetyl-5-methoxytryptamine | -12 |
| 2-oxo-L-threo-hexono-1,4-lactone-2,3-enediol | -17 |
| 6-ethoxy-1,2-dihydro-2,2,4-trimethylquinoline | -64 |

2-2. Production of Protein Composition 1 (Powder)

200 mg of artificial spider silk protein powder (PRT410) obtained in the above refining step was introduced into a sample bottle. A stabilizer-containing powder (powder-form protein composition) (stabilizer content with respect to total amount of dry matter: 0.5% by mass) was prepared in a similar manner as in the item 2-1 except that propyl 3,4,5-trihydroxybenzoate was used as a stabilizer and the content of the stabilizer was adjusted to 0.5% by mass.

As a control, a protein powder was prepared in the same manner as described above except that the stabilizer was not added.

The heat stability was evaluated in a similar manner as in the item 2-1. The calculated value of the Extension of Time at $I_{max}$ [%] was 35%.

3-1. Production of Protein Composition 2 (Film)

0.56 g of artificial spider silk protein powder (PRT410) obtained in the above refining step was introduced into various sample bottles. After dissolving 2.22 g of calcium chloride in a mixed solution of 8.4 mL of distilled water and 6.7 mL of ethanol to create a solvent for dissolving the artificial spider silk protein powder, 5 g of the dissolving solvent was introduced into each sample bottle. The stabilizers shown in Table 5 below were dissolved in ethanol at a concentration of 1.4% by mass. A dope solution was prepared by introducing 100 μL of the stabilizer solution into each sample bottle (amount of stabilizer: 1.12 mg) and stirring at 65° C. for 6 hours.

0.63 g of the prepared dope solution was cast in a polystyrene (PS) petri dish and dried by being left to stand in a state of 60° C. and 550 hPa for 7 days. After drying, each petri dish was immersed for 30 minutes in a mixed solution of acetone and methanol (ratio 7:3). Thereafter, a film is peeled off from the petri dish, immersed in a methanol solution for 30 minutes, and then naturally dried to produce a stabilizer-containing artificial spider silk film with a thickness of 120 μm (stabilizer content ratio with respect to total amount of dry matter: 0.2% by mass).

TABLE 5

| Stabilizer Name |
|---|
| N,N'-hexane-1,6-diyl bis(3-(3,5-di-tert-butyl-4-hydroxyphenylpropionamide)) |
| 1,6-hexanediol bis[3-(3,5-di-tert-butyl-4-hydroxyphenyl)propionate] |
| 6,6'-di-tert-butyl-4,4'-butylidene di-m-cresol |
| 2,6-di-tert-butyl-p-cresol |
| 3,9-bis(2,6-di-tert-butyl-4-methylphenoxy)-2,4,8,10-tetraoxa-3,9-diphosphaspiro[5.5]undecarte |
| Poly[[6-[-[(1,1,3,3-tetramethylbutyl)amino]-1,3,5-triazine-2,4-diyl][(2,2,6,6-tetramethyl-4-piperidinyl)imino]-1,6hexanediyl[(2,2,6,6-tetramethyl-4-piperidinyl)imino]] |
| α-tocopherol |
| Propyl 3,4,5-trihydroxybenzoate |
| 4,4',4"-(1-methylpropanyl-3-ylidene)tris(6-tert-butyl-m-cresol) |
| 2,2'-methylenebis(4,6-di-tert-butylphenyl) 2-ethylhexylphosphite |
| Octadecyl 3-(3,5-di-tert-butyl-4-hydroxyphenyl)propionate |
| Tris(2,4-di-tert-butylphenyl) phosphite |
| 3,9-bis{2-[3-(3-tert-butyl-4-hydroxy-5-methylphenyl)propionyloxy]-1,1-dimethylethyl}-2,4,8,10-tetraoxaspiro[5,5]undecane |

TABLE 5-continued

| Stabilizer Name |
| --- |
| 3-[3-(3,5-ditert-butyl-4-hydroxyphenyl)propanoyloxy]-2,2-bis[3-(3,5-ditert-butyl-4-hydroxyphenyl)propanoyloxymethyl]propyl 3-(3,5-ditert-butyl-4-hydroxyphenyl)propanoate |
| Thiobis[2-(1,1-dimethylethyl)-5-methyl-4,1-phenylene]-bis[3-(dodecylthio)propionate] |
| 1,3,5-tris(3,5-di-tert-butyl-4-hydroxybenzyl)-1,3,5-triazine-2,4,6(1H,3H,5H)-trione |
| 2,2-bis{[3-(dodecylthio)-1-oxopropoxy]methyl}propane-1,3-diyl bis[3-(dodecylthio)propionate] |
| 1,3,5-tris(3,5-di-tert-butyl-4-hydroxyphenylmethyl)-2,4,6-trimethylbenzene |

Heat stability evaluation was performed as follows. The film described above was placed in a chamber for accommodating a sample, and the chamber was set in an apparatus. Thereafter, dry air was circulated at a flow rate of 100 mL/min, maintained at 200° C., and time-dependent changes in chemiluminescence intensity were detected with a chemiluminescence analyzer (CLA-ID2-HS, manufactured by Tohoku Electronic Industrial Co., Ltd.). The Extension of Time at $I_{max}$ [%] was calculated in a similar manner as in the item 2-1 except that the time until the chemiluminescence intensity of the film to which the stabilizer is not added reaches the maximum value was $T_0$, and the time until the chemiluminescence intensity of the stabilizer-containing film reaches the maximum value was $T_1$. The results are shown in Table 6 below.

TABLE 6

| Stabilizer Name | Extension of time at Imax [%] |
| --- | --- |
| N,N'-hexane-1,6-diylbis(3-(3,5-di-tert-butyl-4-hydroxyphenylpropionamide)) | 43 |
| 1,6-hexanediol bis[3-(3,5-di-tert-butyl-4-hydroxyphenyl)propionate] | 33 |
| 6,6'-di-tert-butyl-4,4'-butylidene di-m-cresol | 31 |
| 2,6-di-tert-butyl-p-cresol | 29 |
| 3,9-bis(2,6-di-tert-butyl-4-methylphenoxy)-2,4,8,10-tetraoxa-3,9-diphosphaspiro[5.5]undecane | 26 |
| Pol[[6-[(1,1,3,3-tetramethylbutyl)amino]-1,3,5-triazine-2,4-diyl][(2,2,6,6-tetramethyl-4-piperidinyl)iminol-1,6 hexanediyl[(2,2,6,6-tetramethyl-4-piperidinyl)imino]] | 26 |
| α-tocopherol | 19 |
| Propyl 3,4,5-trihydroxybenzoate | 17 |
| 4,4',4''-(1-methylpropanyl-3-ylidene) tris(6-tert-butyl-m-cresol) | 13 |
| 2,2'-methylenebis(4,6-di-tert-butylphenyl) 2-ethylhexylphosphite | 9 |
| Octadecyl 3-(3,5-di-tert-butyl-4-hydroxyphenyl)propionate | 5 |
| Tris(2,4-di-tert-butylphenyl) phosphite | 4 |
| 3,9-bis{2-[3-(3-tert-butyl-4-hydroxy-5-methylphenyl)propionyloxyl-1,1-dimethylethyl}-2,4,8,10-tetraoxaspiro[5,5]undecane | 4 |
| 3-[3-(3,5-di-tert-butyl-4-hydroxyphenyl)propanoyloxy]-2,2-bis[3-(3,5-di-tert-butyl-4-hydroxyphenyl)propanoyloxymethyl]propyl 3-(3,5-ditert-butyl-4-hydroxyphenyl)propanoate | 0 |
| Thiobis[2-(1,1-dimethylethyl)-5-methyl-4,1-phenylene]-bis[3-(dodecylthio)propionate] | −1 |
| 1,3,5-tris(3,5-di-tert-butyl-4-hydroxybenzyl)-1,3,5-triazine-2,4,6(1H,3H,5H)-trione | −1 |
| 2,2-bis{[3-dodecylthio)-1-oxopropoxy]methyl}propane-1,3-diyl bis[3-(dodecylthio)propionate] | −3 |
| 1,3,5-tris(3,5-di-tert-butyl-4-hydroxyphenylmethyl)-2,4,6-trimethylbenzene | −14 |

3-2. Production of Protein Composition 2 (Film)

Combinations shown in Table 7 below from among the stabilizers shown in Table 5 were used as the stabilizers. A dope solution (stabilizer amount: 2.24 mg) was prepared in a similar manner as in the item 3-1 except that the two types of stabilizers were each dissolved in ethanol at a concentration of 1.4% by mass, and a stabilizer-containing artificial spider silk film with a thickness of 120 m was produced (stabilizer content ratio with respect to total amount of dry matter: 0.4% by mass).

For comparison, a stabilizer-containing artificial spider silk film (stabilizer content ratio with respect to total amount of dry matter: 0.4% by mass) with a thickness of 120 μm was produced in a similar manner as in the item 3-1 except that propyl 3,4,5-trihydroxybenzoate was used alone as a stabilizer and dissolved in ethanol at a concentration of 2.8% by mass.

TABLE 7

| Stabilizer Name |
| --- |
| Propyl 3,4,5-trihydroxybenzoate |
| Propyl 3,4,5-trihydroxybenzoate and 3,9-bis(2,6-di-tert-butyl-4-methylphenoxy)-2,4,8,10-tetraoxa-3,9-diphosphaspiro[5.5]undecane |
| Propyl 3,4,5-trihydroxybenzoate and 2,2'-methylenebis(4,6-di-tert-butylphenyl) 2-ethylhexylphosphite |
| Propyl 3,4,5-trihydroxybenzoate and thiobis[2-(1,1-dimethylethyl)-5-methyl-4,1-phenylene]-bis[3-(dodecylthio)propionate] |

Heat stability evaluation was performed with a similar procedure as in the item 3-1 and the Extension of Time at $I_{max}$ [%] was calculated. The results are shown in Table 8 below.

TABLE 8

| Stabilizer Name | Extension of time at Imax [%] |
| --- | --- |
| Propyl 3,4,5-trihydroxybenzoate | 41 |
| Propyl 3,4,5-trihydroxybenzoate and 3,9-bis(2,6-di-tert-butyl-4-methylphenoxy)-2,4,8,10-tetraoxa-3,9-diphosphaspiro[5.5]undecane | 40 |
| Propyl 3,4,5-trihydroxybenzoate and 2,2'-methylenebis(4,6-di-tert-butylphenyl) 2-ethylhexylphosphite | 48 |
| Propyl 3,4,5-trihydroxybenzoate and thiobis[2-(1,1-dimethylethyl)-5-methyl-4,1-phenylene]-bis [3-(dodecylthio)propionate] | 40 |

As shown in Table 8, a stabilizer-containing artificial spider silk film produced using two types of stabilizers of propyl 3,4,5-trihydroxybenzoate and 2,2'-methylenebis(4,6-di-tert-butylphenyl) 2-ethylhexylphosphite exhibits higher heat stability than stabilizer-containing artificial spider silk films produced using propyl 3,4,5-trihydroxybenzoate alone.

3-3. Production of Protein Composition 2 (Film)

A stabilizer-containing artificial spider silk film (stabilizer content ratio with respect to total amount of dry matter: 0.4% by mass) with a thickness of 120 μm was produced in a similar manner as in the item 3-2 except that the stabilizer was used in the combination shown in Table 9 below.

For comparison, a stabilizer-containing artificial spider silk film (stabilizer content ratio with respect to total amount of dry matter: 0.4% by mass) with a thickness of 120 μm was produced in the same manner as the item 3-2 except that 6,6'-di-tert-butyl-4,4'-butylidene di-m-cresol was used alone as a stabilizer.

TABLE 9

Stabilizer Name 6,6'-di-tert-butyl-4,4'-butylidene di-m-cresol
6,6'-di-tert-butyl-4,4'-butylidene di-m-cresol, and
3,9-bis(2,6-di-tert-butyl-4-methylphenoxy)-2,4,8,10-tetraoxa-3,9-
diphosphaspiro[5.5]undecane
6,6'-di-tert-butyl-4,4'-butylidene di-m-cresol, and
2,2'-methylenebis(4,6-di-tert-butylphenyl)2-ethylenehexylphosphite
6,6'-di-tert-butyl-4,4'-butylidene di-m-cresol, and
thiobis[2-(1,1-dimethylethyl)-5-methyl-4,1-phenylene]bis[3-
(dodecylthio)propionate]

The heat stability evaluation was performed with a similar procedure as in the item 3-1 and the Extension of Time at $I_{max}$ [%] was calculated. The results are shown in Table 10 below.

TABLE 10

| Stabilizer Name | Extension of time at Imax [%] |
|---|---|
| 6,6'-di-tert-butyl-4,4'-butylidene di-m-cresol | 38 |
| 6,6'-di-tert-butyl-4,4'-butylidene di-m-cresol, and 3,9-bis(2,6-di-tert-butyl-4-methylphenoxy)-2,4,8,10-tetraoxa-3,9-diphosphaspiro[5.5]undecane | 24 |
| 6,6'-di-tert-butyl-4,4'-butylidene di-m-cresol, and 2,2'-methylenebis(4,6-di-tert-butylphenyl)2-ethylenehexylphosphite | 33 |
| 6,6'-di-tert-butyl-4,4'-butylidene di-m-cresol, and thiobis[2-(1,1-dimethylethyl)-5-methyl-4,1-phenylene]-bis[3-(dodecylthio)propionate] | 44 |

As shown in Table 10, a stabilizer-containing artificial spider silk film produced using two types of stabilizers of 6,6'-di-tert-butyl-4,4'-butylidene di-m-cresol and thiobis[2-(1,1-dimethylethyl)-5-methyl-4,1-phenylene]-bis[3-(dodecylthio) propionate exhibited higher heat stability than a stabilizer-containing artificial spider silk film produced using 6,6'-di-tert-butyl-4,4'-butylidene di-m-cresol alone.

3-4. Production of Protein Composition 2 (Film)

A stabilizer-containing artificial spider silk film (stabilizer content ratio with respect to total amount of dry matter: 0.4% by mass) with a thickness of 120 μm was produced in a similar manner as in the item 3-2 except that the stabilizer was used in the combination shown in Table 11 below.

For comparison, a stabilizer-containing artificial spider silk film (stabilizer content ratio with respect to total amount of dry matter: 0.4% by mass) with a thickness of 120 μm was produced in a similar manner as in the item 3-2 except that N,N'-hexane-1,6-diyl bis(3-(3,5-di-tert-butyl-4-hydroxyphenylpropionamide)) was used alone as a stabilizer.

TABLE 11

Stabilizer Name

N,N'-hexane-1,6-diyl
bis(3-(3,5-di-tert-butyl-4-hydroxyphenylpropionamide))
N,N'-hexane-1,6-diyl
bis(3-(3,5-di-tert-butyl-4-hydroxyphenylpropionamide)), and
3,9-bis(2,6-di-tert-butyl-4-methylphenoxy)-2,4,8,10-tetraoxa-3,9-
diphosphaspiro[5.5]undecane
N,N'-hexane-1,6-diyl
bis(3-(3,5-di-tert-butyl-4-hydroxyphenylpropionamide)), and
2,2'-methylenebis(4,6-di-tert-butylphenyl) 2-ethylhexylphosphite

TABLE 11-continued

Stabilizer Name

N,N'-hexane-1,6-diyl
bis(3-(3,5-di-tert-butyl-4-hydroxyphenylpropionamide)), and
thiobis[2-(1,1-dimethylethyl)-5-methyl-4,1-phenylene]-bis[3-
(dodecylthio)propionate]

The heat stability evaluation was performed with a similar procedure as in the item 3-1 and the Extension of Time at $I_{max}$ [%] was calculated. The results are shown in Table 12 below.

TABLE 12

| Stabilizer Name | Extension of time at Imax [%] |
|---|---|
| N,N'-hexane-1,6-diyl bis(3-(3,5-di-tert-butyl-4-hydroxyphenylpropionamide)) | 36 |
| N,N'-hexane-1,6-diyl bis(3-(3,5-di-tert-butyl-4-hydroxyphenylpropionamide)), and 3,9-bis(2,6-di-tert-butyl-4-methylphenoxy)-2,4,8,10-tetraoxa-3,9-diphosphaspiro[5.5]undecane | 6 |
| N,N'-hexane-1,6-diyl bis(3-(3,5-di-tert-butyl-4-hydroxyphenylpropionamide)), and 2,2'-methylenebis(4,6-di-tert-butylphenyl) 2-ethylhexylphosphite | 52 |
| N,N'-hexane-1,6-diyl bis(3-(3,5-di-tert-butyl-4-hydroxyphenylpropionamide)), and thiobis[2-(1,1-dimethylethyl)-5-methyl-4,1-phenylene]-bis[3-(dodecylthio)propionate] | 18 |

As shown in Table 12, a stabilizer-containing artificial spider silk film produced using two types of stabilizers of N,N'-hexane-1,6-diyl bis(3-(3,5-di-tert-butyl-4-hydroxyphenylpropionamide)) and 2,2'-methylenebis(4,6-di-tert-butylphenyl) 2-ethylhexylphosphite exhibited a higher heat stability than a stabilizer-containing artificial spider silk film produced using N,N'-hexane-1,6-diyl bis(3-(3,5-di-tert-butyl-4-hydroxyphenylpropionamide)) alone.

3-5. Production of Protein Composition 2 (Film)

A stabilizer-containing artificial spider silk film (stabilizer content ratio with respect to total amount of the dry matter: 0.4% by mass) with a thickness of 120 μm was produced in a similar manner as in the item 3-2 except that the stabilizer was used in the combination shown in Table 13 below.

For comparison, a stabilizer-containing artificial spider silk film (stabilizer content ratio with respect to total amount of dry matter: 0.4% by mass) with a thickness of 120 μm was produced in a similar manner as in the item 3-2 except that poly[[6-[(1,1,33-tetramethylbutyl)amino]-1,3,5-triazine-2,4-diyl][(2,2,6,6-tetramethyl-4-piperidinyl)imino]-1,6-hexanediyl[(2,2,6,6-tetramethyl-4-piperidinyl)imino]] was used alone as a stabilizer

TABLE 13

Stabilizer Name

Poly[[6-[(1,1,3,3-tetramethylbutyl)amino]-1,3,5-triazine-2,4-diyl]
[(2,2,6,6-tetramethyl-4-piperidinyl)imino]-1,6hexanediyl[(2,2,6,6-
tetramethyl-4-piperidinyl)imino]]
Poly[[6-[(1,1,3,3-tetramethylbutyl)amino]-1,3,5-triazine-2,4-diyl]
[(2,2,6,6-tetramethyl-4-piperidinyl)imino]-1,6hexanediyl[(2,2,6,6-
tetramethyl-4-piperidinyl)imino]], and
3,9-bis(2,6-di-tert-butyl-4-methylphenoxy)-2,4,8,10-tetraoxa-3,9-
diphosphaspiro[5.5]undecane TABLE 13-continued Stabilizer Name Poly[[6-[(1,1,3,3-tetramethylbutyl)amino]-1,3,5-triazine-2,4-diyl]
[(2,2,6,6-tetramethyl-4-piperidinyl)imino]-1,6hexanediyl[(2,2,6,6-
tetramethyl-4-piperidinyl)imino]]), and
2,2'-methylenebis(4,6-di-tert-butylphenyl) 2-ethylhexylphosphite
Poly[[6-[(1,1,3,3-tetramethylbutyl)amino]-1,3,5-triazine-2,4-diyl]
[(2,2,6,6-tetramethyl-4-piperidinyl)imino]-1,6hexanediyl[(2,2,6,6-
tetramethyl-4-piperidinyl)imino
thiobis[2-(1,1-dimethylethyl)-5-methyl-4,1-phenylene]-bis[3-
(dodecylthio)propionate]

The heat stability evaluation was performed with a similar procedure as in the item 3-1. described above and the Extension of Time at $I_{max}$ [%] was calculated. The results are shown in Table 14 below.

TABLE 14

| Stabilizer Name | Extension of time at Imax [%] |
|---|---|
| Poly[[6-[(1,1,3,3-tetramethylbutyl)aminol-1,3,5-triazine-2,4-diyl][2,2,6,6-tetramethyl-4-piperidinyl)imino]-1,6 hexanediyl[(2,2,6,6-tetramethyl-4-piperidinyl)imino]] | 33 |
| Poly[[6-[(1,1,3,3-tetramethylbutyl)aminol-1,3,5-triazine-2,4-diyl][(2,2,6,6-tetramethyl-4-piperidinyl)imino]-1,6 hexanediyl[(2,2,6,6-tetramethyl-4-piperidinyl)imino]], and 3,9-bis(2,6-di-tert-butyl-4-methylphenoxy)-2,4,8,10-tetra oxa-3,9-diphosphaspiro[5.5]undecane | 41 |
| Poly[[6-[(1,1,3,3-tetramethylbutyl)aminol-1,3,5-triazine-2,4-diyl][(2,2,6,6-tetramethyl-4-piperidinyl)imino]-1,6 hexanediyl[(2,2,6,6-tetramethyl-4-piperidinyl)imino]], and 2,2'-methylenebis(4,6-di-tert-butylphenyl) 2-ethylhexylphosphite | 44 |
| Poly[[6-[(1,1,3,3-tetramethylbutyl)aminol-1,3,5-triazine-2,4-diyl][(2,2,6,6-tetramethyl-4-piperidinyl)imino]-1,6 hexanediyl[(2,2,6,6-tetramethyl-4-piperidinyl)imino]], and thiobis[2-(1,1-dimethylethyl)-5-methyl-4,1-phenylene[-bis[3-(dodecylthio)propionate] | 60 |

As shown in Table 14, stabilizer-containing artificial spider silk films produced using any two types of stabilizers of poly[[6-[(1,1,3,3-tetramethylbutyl)amino]-1,3,5-triazine-2,4-diyl][(2,2,6,6-tetramethyl-4-piperidinyl)imino]-1,6-hexanediyl[(2,2,6,6-tetramethyl-4-piperidinyl)imino]], and 3,9-bis(2,6-di-tert-butyl-4-methylphenoxy)-2,4,8,10-tetraoxa-3,9-diphosphaspiro[5.5]undecane, 2,2'-methylenebis(4,6-di-tert-butylphenyl) 2-ethylhexylphosphite or thiobis[2-(1,1-dimethylethyl)-5-methyl-4,1-phenylene]-bis[3-(dodecylthio)propionate] exhibited higher heat stability than a stabilizer-containing artificial spider silk film produced using poly[[6-[(1,1,3,-tetramethylbutyl)amino]-1,3,5-triazine-2,4-diyl][(2,2,6,6-tetramethyl-4-piperidinyl)imino]-1,6-hexanediyl[(2,2,6,6-tetramethyl-4-piperidinyl)imino]] alone.

4-1. Production of Protein Composition 1 (Molded Article)

9.98 g of artificial spider silk protein powder (PRT410) obtained in the refining step described above was introduced into a vial. As a stabilizer, propyl 3,4,5-trihydroxybenzoate was dissolved in ethanol at a concentration of 1 mg/mL, and this stabilizer solution was introduced into a 20 mL vial (stabilizer amount: 20 mg). Then, the vial was sealed and ultrasonic stirring was performed for 60 minutes at room temperature. Furthermore, after stirring for 60 hours, drying was carried out under reduced pressure at 40° C. for 4 hours to evaporate the solvent to prepare a stabilizer-containing powder (stabilizer content ratio with respect to total amount of dry matter: 0.2% by mass).

The stabilizer-containing powder was milled with a mill (IFM-80, manufactured by Iwatani Corporation) to adjust the particle diameter, and then 1.35 g of the stabilizer-containing powder (referred to below as "protein composition") after particle diameter adjustment was weighed out and this protein composition was introduced into the through hole of the mold 2 (a cylindrical shape mold having a rectangular through hole with a cross-section of 35 mm×15 mm) of the press molding machine 10 shown in FIG. 1. At this time, the protein composition was added to make the thickness even. After introducing all of the protein composition, heating of the mold 2 was started, and the upper pin 4 and the lower pin 6 were inserted into the through holes using a hand press (NT-100H-V09, manufactured by NPa System Co., Ltd.) to press the protein composition. At this time, the pressing condition of the protein composition was controlled to be 40 kN. Heating was stopped when the temperature of the protein composition reached 200° C., the protein composition was naturally cooled and taken out when the temperature of the protein composition reached 50° C. and, after performing deburring, a stabilizer-containing molded article having a 35 mm×15 mm×2 mm rectangular parallelepiped shape was obtained (stabilizer content ratio with respect to total amount of dry matter: 0.2% by mass).

In addition, 9.95 g of the artificial spider silk protein powder (PRT410) obtained in the refining step described above was introduced into a vial. As a stabilizer, propyl 3,4,5-trihydroxybenzoate was dissolved in ethanol at a concentration of 2.5 mg/mL, and the stabilizer solution was introduced into a 20 mL vial (stabilizer amount: 50 mg). Otherwise, a stabilizer-containing molded article having a 35 mm×15 mm×2 mm rectangular parallelepiped shape was obtained with the same procedure as described above (stabilizer content ratio with respect to total amount of dry matter: 0.5% by mass).

For comparison, 10 g of artificial spider silk protein powder (PRT410) obtained in the above refining step was introduced into a vial, and then 20 mL of ethanol was introduced (a stabilizer was not added). Otherwise, with the same procedure as described above, a molded article having a 35 mm×15 mm×2 mm rectangular parallelepiped shape was obtained.

With respect to heat stability, a bending test was performed to evaluate the strength of the article. That is, after leaving the obtained molded article to stand in a constant temperature and humidity chamber (LHL-113, manufactured by Espec Corp.) for 1 day under conditions of 20° C./65% RH, a three-point bending test was performed using a jig in an autograph (AG-Xplus, manufactured by Shimadzu Corporation). The load cell used was 50 kN. At this time, the distance between the support points for three-point bending was fixed to 27 mm, and the measurement rate was set to 1 mm/minute. In addition, the size of the molded article was measured with a micro caliper, placed in the jig, and tested. The results are shown in Table 15 below.

TABLE 15

| | Stabilizer content ratio 0 [% by mass] | Stabilizer content ratio 0.2 [% by mass] | Stabilizer content ratio 0.5 [% by mass] |
|---|---|---|---|
| Bending strength [MPa] | 64.38 | 78.34 | 71.49 |

4-2. Production of Protein Composition 1 (Molded Article)

1.35 g of a stabilizer-containing powder (referred to below as a "protein composition") prepared in a similar manner as in the item 4-1 was weighed out and introduced into the through hole of the mold 2 (FIG. 1) (stabilizer content ratio with respect to total amount of dry matter. 0.2% by mass). A stabilizer-containing molded article (stabilizer content ratio with respect to total amount of dry matter: 0.2% by mass) was obtained with a similar procedure as in the item 4-1 except that the heating of the protein composition was stopped after being maintained for 5 minutes when the temperature of the protein composition reached 130° C.

For comparison, 10 g of the artificial spider silk protein powder (PRT410) obtained in the refining step described above was introduced into a vial, and then 20 mL of ethanol was introduced thereto. Otherwise, a molded article was obtained in a similar manner as in the item 4-1 (a stabilizer was not added).

Regarding heat stability, a bending test was performed to evaluate the strength of the article in a similar manner as in the item 4-1. The results are shown in Table 16 below.

TABLE 16

|  | Stabilizer content ratio 0 [% by mass] | Stabilizer content ratio 0.2 [% by mass] |
| --- | --- | --- |
| Bending strength [MPa] | 70.56 | 74.4 |

As shown in Table 16, in comparison with a molded article produced without adding a stabilizer, the stabilizer-containing molded article produced by adding propyl 3,4,5-trihydroxybenzoate exhibited higher heat stability.

4-3. Production of Protein Composition 1 (Molded Article)

As a stabilizer, 6,6'-di-tert-butyl-4,4'-butylidene di-m-cresol was dissolved in ethanol at a concentration of 1 mg/mL, and this stabilizer solution was introduced into a 30 mL vial (stabilizer amount: 30 mg). 9.97 g of artificial spider silk protein powder (PRT410) obtained in the above refining step was introduced into a vial. The vial was sealed and stirring was performed overnight at room temperature using a commercially available magnetic stirrer. The dispersion liquid was transferred to a container without a lid and left to stand in a draft for 3 days to volatilize and remove the ethanol, and then dried under reduced pressure at 35° C. for several hours to prepare a stabilizer-containing powder (powder-form protein composition) (referred to below as a "protein composition"). 1.35 g of the protein composition was weighed out and introduced into the through holes of the mold 2 (FIG. 1). Heating of the protein composition was stopped after being maintained for 5 minutes when the temperature of the protein composition reached 190° C. Otherwise, in a similar manner as in the item 4-1, a stabilizer-containing molded article having a 35 mm×15 mm×2 mm rectangular parallelepiped shape was obtained (stabilizer content ratio with respect to total amount of dry matter: 0.3% by mass).

For comparison, 10 g of the artificial spider silk protein powder (PRT410) obtained in the refining step described above was introduced into a vial, and then 30 mL of ethanol was introduced thereto. Otherwise, in a similar manner as in the item 4-1, a molded article with a rectangular parallelepiped shape of 35 mm×15 mm×2 mm was obtained (without adding a stabilizer).

Regarding heat stability, a bending test was performed in a similar manner as the item 4-1 and the strength of the article was evaluated. The results are shown in Table 17 below.

TABLE 17

|  | Stabilizer content ratio 0 [% by mass] | Stabilizer content ratio 0.3 [% by mass] |
| --- | --- | --- |
| Bending strength [MPa] | 84.9 | 98.0 |

As shown in Table 17, in comparison with a molded article produced without adding a stabilizer, a stabilizer-containing molded article produced by adding 6,6'-di-tert-butyl-4,4'-butylidene di-m-cresol exhibited higher heat stability.

5. Production of Protein Composition 2 (Fiber)

<Preparation of Dope Solution>

As a solvent, dimethyl sulfoxide (LiCl/DMSO) in which LiCl was dissolved at a concentration of 4% by mass was prepared. 3.5 g of dry powder of the artificial spider silk protein powder (PRT410) obtained in the above refining step was weighed and introduced into a vial. A LiCl/DMSO solvent was added so as to have a concentration of 24% by mass, and, while stirring using a mechanical stirrer, the solution was heated to cause dissolution at 90° C., and cooled to 60° C. to prepare a protein solution.

The 2-propanol was introduced into another vial and dissolved by adding propyl 3,4,5-trihydroxybenzoate as a stabilizer to prepare a stabilizer solution. The prepared stabilizer solution was added to the above protein solution. While stirring the mixed solution using a mechanical stirrer, the solution was heated to 90° C. for dissolution to prepare a stabilizer-containing dope solution. The stabilizer content ratio of the stabilizer-containing dope solution was 0.2% by mass, 0.5% by mass, 1.0% by mass, and 4.0% by mass, respectively.

For comparison, a dope solution including no stabilizer was prepared. 3.5 g of dry powder of the artificial spider silk protein powder (PRT410) obtained in the above refining step was weighed and introduced into a vial. The LiCl/DMSO solvent described above was added so as to have a concentration of 24% by mass and a dope solution was prepared in the same manner as described above (without adding a stabilizer).

<Spinning>

The obtained stabilizer-containing a dope solution was subjected to dry and wet spinning under the following conditions using a known spinning device, and the formed fiber was dried and then wound to produce the protein composition 2 (fiber). The dry and wet spinning conditions were as follows.

Coagulation liquid: Methanol
Total extension ratio: 5 times
Drying temperature: 60° C.

<Heat Stability Evaluation>

The heat stability evaluation was performed as follows. The stabilizer-containing protein fiber was placed in a chamber for accommodating a sample, and the chamber was set in an apparatus. Thereafter, dry air was circulated at a flow rate of 100 mL/min, maintained at 190° C., and time-dependent changes in chemiluminescence intensity were detected by a chemiluminescence analyzer (CLA-ID2-HS manufactured by Tohoku Electronic Industrial Co., Ltd.). The time until the chemiluminescence intensity of the protein fiber to which the stabilizer was not added reaches the maximum value was $T_0$, and the time until the chemiluminescence intensity of the stabilizer-containing protein fiber reaches the maximum value was $T_1$, and the Extension of Time at $I_{max}$ was calculated according to the following equation.

$$(T_1-T_0)/T_0\times 100[\%]$$

The results are shown in Table 18 below.

TABLE 18

| | Stabilizer content ratio 0.2 [% by mass] | Stabilizer content ratio 0.5 [% by mass] | Stabilizer content ratio 1.0 [% by mass] | Stabilizer content ratio 4.0 [% by mass] |
|---|---|---|---|---|
| Extension of time at Imax [%] | 51 | 99 | 80 | 18 |

As shown in Table 18, the highest heat stability was exhibited in the stabilizer-containing protein fiber produced using the stabilizer-containing dope solution having a stabilizer content ratio of 0.5% by mass.

REFERENCE SIGNS LIST

2: DIE, 4: UPPER SIDE PIN, 6: LOWER SIDE PIN, 8a: PROTEIN COMPOSITION BEFORE HOT PRESSING, 8b: PROTEIN COMPOSITION AFTER HOT PRESSING, 10: PRESS MOLDING MACHINE

Sequence Listing

The invention claimed is:

1. A protein composition comprising:
dry matter of a dispersion in which a structural protein is dispersed in a stabilizer solution, wherein the stabilizer comprises at least one type selected from the group consisting of a catechol-based stabilizer, 6-hydroxy-2,5,7,8-tetramethylchroman-2-carboxylic acid, 2,6-di-tert-butyl-p-cresol, and 2-tert-butyl-4-methoxyphenol.

2. The protein composition according to claim 1, wherein the catechol-based stabilizer comprises 2-(3,4-dihydroxyphenyl)-3,5,7-trihydroxy-4H-chromen-4-one, (1S,3R,4R,5R)-3-{[3-(3,4-dihydroxyphenyl)acryloyl]oxy}-1,4,5-trihydroxycyclohexane-1-carboxylic acid, 2-(3,4-dihydroxyphenyl)-5,7-dihydroxy-3-{[(2S,3R,4S,5S,6R)-3,4,5-trihydroxy-6-({[(2R,3R,4R,5R,6S)-3,4,5-trihydroxy-6-methyloxan-2-yl]oxy}methyl)oxan-2-yl]oxy}-4H-chromen-4-one, propyl 3,4,5-trihydroxybenzoate or 4,4'-(2,3-dimethylbutane-1,4-diyl)dibenzene-1,2-diol.

3. The protein composition according to claim 1, which is in powder form.

4. The protein composition according to claim 1, which is a molded article.

5. A protein composition comprising:
dry matter of a solution in which a structural protein and a stabilizer are dissolved,
wherein the stabilizer comprises at least one type selected from the group consisting of N,N'-hexane-1,6-diyl bis[3-(3,5-di-tert-butyl-4-hydroxyphenyl)propionamide], 1,6-hexanediol bis[3-(3,5-di-tert-butyl-4-hydroxyphenyl)propionate], 2,6-di-tert-butyl-p-cresol, 3,9-bis(2,6-di-tert-butyl-4-methylphenoxy)-2,4,8,10-tetraoxa-3,9-diphosphaspiro[5.5]undecane, poly[[6-[(1,1,3,3-tetramethylbutyl)amino]-1,3,5-triazine-2,4-diyl][(2,2,6,6-tetramethyl-4-piperidinyl)imino]-1,6-hexanediyl[(2,2,6,6-tetramethyl-4-piperidinyl)imino]], propyl 3,4,5-trihydroxybenzoate and 4,4',4"-(1-methylpropanyl-3-ylidene) tris(6-tert-butyl-m-cresol).

6. The protein composition according to claim 5, wherein the stabilizer comprises:
any one type selected from the group consisting of 3,9-bis(2,6-di-tert-butyl-4-methylphenoxy)-2,4,8,10-tetraoxa-3,9-diphosphaspiro[5.5]undecane, 2,2'-methylenebis(4,6-di-tert-butylphenyl) 2-ethylhexylphosphite, and thiobis[2-(1,1-dimethylethyl)-5-methyl-4,1-phenylene]-bis[3-(dodecylthio)propionate], and
poly[[6-[(1,1,3,3-tetramethylbutyl)amino]-1,3,5-triazine-2,4-diyl][(2,2,6,6-tetramethyl-4-piperidinyl)imino]-1,6-hexanediyl[(2,2,6,6-tetramethyl-4-piperidinyl)imino]]].

7. The protein composition according to claim 5, wherein the stabilizer comprises thiobis[2-(1,1-dimethylethyl)-5-methyl-4,1-phenylene]-bis[3-(dodecylthio)propionate].

8. The protein composition according to claim 5, wherein the stabilizer comprises N,N'-hexane-1,6-diyl bis[3-(3,5-di-tert-butyl-4-hydroxyphenyl)propionamide] and 2,2'-methylenebis(4,6-di-tert-butylphenyl) 2-ethylhexylphosphite.

9. The protein composition according to claim 5, which is not in powder form.

10. The protein composition according to claim 5, wherein the stabilizer is more than 0 parts by mass and 10 parts by mass or less with respect to 100 parts by mass of the protein.

11. A method for producing a structural protein composition, comprising:

a step of obtaining a dispersion by dispersing a structural protein in a stabilizer solution; and
a step of obtaining dry matter by removing volatile components from the dispersion,
wherein the stabilizer comprises at least one type selected from the group consisting of a catechol-based stabilizer, 6-hydroxy-2,5,7,8-tetramethylchroman-2-carboxylic acid, 2,6-di-tert-butyl-p-cresol, and 2-tert-butyl-4-methoxyphenol.

12. A method for producing a structural protein composition, comprising:
a step of obtaining a mixed solution by mixing a structural protein, a solvent for dissolving the structural protein, and a stabilizer solution; and
a step of obtaining dry matter by removing volatile components from the mixed solution,
wherein the stabilizer includes at least one type selected from the group consisting of N,N'-hexane-1,6-diyl bis[3-(3,5-di-tert-butyl-4-hydroxyphenyl)propionamide], 1,6-hexanediol bis[3-(3,5-di-tert-butyl-4-hydroxyphenyl)propionate], 2,6-di-tert-butyl-p-cresol, 3,9-bis(2,6-di-tert-butyl-4-methylphenoxy)-2,4,8,10-tetraoxa-3,9-diphosphaspiro[5.5]undecane, poly[[6-[(1,1,3,3-tetramethylbutyl)amino]-1,3,5-triazine-2,4-diyl][(2,2,6,6-tetramethyl-4-piperidinyl)imino]-1,6-hexanediyl[(2,2,6,6-tetramethyl-4-piperidinyl)imino]], propyl 3,4,5-trihydroxybenzoate and 4,4',4"-(1-methylpropanyl-3-ylidene)tris(6-tert-butyl-m-cresol).

13. The method according to claim 12, wherein the stabilizer comprises thiobis[2-(1,1-dimethylethyl)-5-methyl-4,1-phenylene]-bis[3-(dodecylthio)propionate].

14. The method according to claim 12, wherein the stabilizer comprises N,N'-hexane-1,6-diyl bis[3-(3,5-di-tert-butyl-4-hydroxyphenyl)propionamide] and 2,2'-methylenebis(4,6-di-tert-butylphenyl) 2-ethylhexylphosphite.

15. A method for improving heat stability of a structural protein, comprising:
obtaining a dispersion by dispersing the structural protein in a solution in which at least one type of compound selected from the group consisting of a catechol-based stabilizer, 6-hydroxy-2,5,7,8-tetramethylchroman-2-carboxylic acid, 2,6-di-tert-butyl-p-cresol, and 2-tert-butyl-4-methoxyphenol is dissolved, and obtaining dry matter in which the structural protein and the compound are both present by removing volatile components from the dispersion.

16. A method for improving heat stability of a structural protein, comprising:
obtaining a mixed solution by mixing
the structural protein,
a solvent for dissolving the structural protein, and
a solution of at least one compound selected from the group consisting of N,N'-hexane-1,6-diyl bis[3-(3,5-di-tert-butyl-4-hydroxyphenyl)propionamide], 1,6-hexanediol bis[3-(3,5-di-tert-butyl-4-hydroxyphenyl)propionate], 2,6-di-tert-butyl-p-cresol, 3,9-bis(2,6-di-tert-butyl-4-methylphenoxy)-2,4,8,10-tetraoxa-3,9-diphosphaspiro[5.5]undecane, poly[[6-[(1,1,3,3-tetramethylbutyl)amino]-1,3,5-triazine-2,4-diyl][(2,2,6,6-tetramethyl-4-piperidinyl)imino]-1,6-hexanediyl[(2,2,6,6-tetramethyl-4-piperidinyl)imino]], propyl 3,4,5-trihydroxybenzoate, and 4,4',4"-(1-methylpropanyl-3-ylidene) tris(6-tert-butyl-m-cresol);

removing volatile components from the mixed solution; and obtaining dry matter in which the structural protein and the compound are both present.

* * * * *